United States Patent
Shimmura et al.

(10) Patent No.: US 12,350,294 B2
(45) Date of Patent: Jul. 8, 2025

(54) MEDIUM COMPRISING SERUM REPLACEMENT, IGF1, STAT3 ACTIVATOR AND ADRENAL GLAND HORMONE WITHOUT BFGF OR ROCK INHIBITOR FOR PRODUCING CORNEAL ENDOTHELIAL SUBSTITUTE CELLS FROM iPS CELLS AND A METHOD THEREOF

(71) Applicant: KEIO UNIVERSITY, Tokyo (JP)

(72) Inventors: Shigeto Shimmura, Tokyo (JP); Shin Hatou, Tokyo (JP); Kazuo Tsubota, Tokyo (JP)

(73) Assignee: KEIO UNIVERSITY, Tokyo (JP)

( * ) Notice: Subject to any disclaimer, the term of this patent is extended or adjusted under 35 U.S.C. 154(b) by 75 days.

(21) Appl. No.: 16/962,590

(22) PCT Filed: Jan. 16, 2019

(86) PCT No.: PCT/JP2019/001142
§ 371 (c)(1),
(2) Date: Jul. 16, 2020

(87) PCT Pub. No.: WO2019/142833
PCT Pub. Date: Jul. 25, 2019

(65) Prior Publication Data
US 2020/0397826 A1  Dec. 24, 2020

(30) Foreign Application Priority Data
Jan. 16, 2018 (JP) .................................. 2018-005076

(51) Int. Cl.
| | |
|---|---|
| C12N 5/07 | (2010.01) |
| A61K 35/30 | (2015.01) |
| A61P 27/02 | (2006.01) |
| C07K 14/54 | (2006.01) |
| C07K 14/57 | (2006.01) |
| C07K 14/65 | (2006.01) |
| C12N 5/00 | (2006.01) |
| C12N 5/071 | (2010.01) |
| C12N 5/074 | (2010.01) |
| C12N 5/079 | (2010.01) |

(52) U.S. Cl.
CPC .............. *A61K 35/30* (2013.01); *A61P 27/02* (2018.01); *C12N 5/0621* (2013.01)

(58) Field of Classification Search
CPC .............. C12N 5/0621; C12N 2500/84; C12N 2501/105; C12N 2501/117; C12N 2501/15; C12N 2501/2306; C12N 2506/45; C12N 5/0018; C12N 5/0696; C12N 2500/25; C12N 2500/90; C12N 2501/237; C12N 2506/02; C12N 5/0623; C07K 14/503
See application file for complete search history.

(56) References Cited

U.S. PATENT DOCUMENTS

| | | | | |
|---|---|---|---|---|
| 9,347,042 | B2 * | 5/2016 | Shimmura | ............... A61P 27/02 |
| 9,752,118 | B2 * | 9/2017 | McCabe | ............. A61L 27/3839 |
| 10,501,725 | B2 * | 12/2019 | Shimmura | ............... C12N 5/10 |
| 2014/0315305 | A1 * | 10/2014 | Shimmura | .......... A61L 27/3808 |
| | | | | 435/377 |
| 2014/0370007 | A1 * | 12/2014 | McCabe | ............. A61L 27/3808 |
| | | | | 424/278.1 |
| 2017/0258495 | A1 * | 9/2017 | Yuan | .................... C12N 5/0609 |
| 2017/0340677 | A1 * | 11/2017 | Shimmura | ........... A61K 31/203 |
| 2019/0083543 | A1 | 3/2019 | Kinoshita et al. | |
| 2019/0119633 | A1 * | 4/2019 | Zhao | .................... C12N 5/0696 |
| 2021/0046124 | A1 | 2/2021 | Kinoshita et al. | |

FOREIGN PATENT DOCUMENTS

| | | |
|---|---|---|
| JP | 2015-155400 A | 8/2015 |
| JP | 6041270 B2 | 12/2016 |
| WO | WO 2003/100026 A2 | 12/2003 |
| WO | WO 2013/051722 A1 | 4/2013 |
| WO | WO 2016/093359 A1 | 6/2016 |
| WO | WO 2017/141926 A1 | 8/2017 |

OTHER PUBLICATIONS

Yadav et al., J. Biol. Chem. 2005; 31830-31840.*
Weston et al., Renal Failure, 2004; 26:1:13-20. DOI:10.1081/JDI-120028538.*
Hatou et al. Inflammation and Regeneration, 2019; 39:19. doi.org/10.1186/s41232-019-0108-y.*
Hatou et al., Stem Cell Res. 2021; 102497. doi.org/10.1016/j.scr.2021.102497.*
Hatou et al., Stem Cell Research, 2021; 55:102497.*
Mikhailova et al., "Small-Molecule Induction Promotes Corneal Epithelial Cell Differentiation from Human Induced Pluripotent Stem Cells," *Stem Cell Rep.*, 2(2): 219-231 (2014).
European Patent Office, Extended European Search Report in European Patent Application No. 19741620.9 (Aug. 18, 2021).
Bajpai et al., "Molecular stages of rapid and uniform neuralization of human embryonic stem cells," *Cell Death Differ.*, 16(6): 807-825 (2009).
Bajpai et al., "CHD7 cooperates with PBAF to control multipotent neural crest formation," *Nature*, 463(7283): 958-962 (2010).

(Continued)

*Primary Examiner* — Chang-Yu Wang
(74) *Attorney, Agent, or Firm* — Leydig, Voit & Mayer, Ltd.

(57) ABSTRACT

Using the medium of the present invention for inducing a cornea endothelial substitute cell from an iPS cell, the medium containing an insulin-like growth factor and a STAT3 activator, and not containing a basic fibroblast growth factor or a ROCK inhibitor, and the method of the present invention for inducing corneal endothelial substitute cells from iPS cells by using the medium, it becomes possible to efficiently produce corneal endothelial substitute cells, particularly to efficiently produce corneal endothelial substitute cells from iPS cells. Furthermore, it becomes possible to stably produce large amounts of corneal endothelial substitute cells by inducing differentiation of iPS cells into corneal endothelial substitute cells more efficiently.

14 Claims, 11 Drawing Sheets
Specification includes a Sequence Listing.

(56) References Cited

OTHER PUBLICATIONS

Chen et al., "Treatment with retinoic acid and lens epithelial cell-conditioned medium in vitro directed the differentiation of pluripotent stem cells towards corneal endothelial cell-like cells," *Exp. Ther. Med.*, 9(2): 351-360 (2015).
Fujii et al., "Immunological Properties of Neural Crest Cells Derived from Human Induced Pluripotent Stem Cells," *Stem Cells Dev.*, 28(1): 28-43 (2019).
Hatou et al., "Functional Corneal Endothelium Derived from Corneal Stroma Stem Cells of Neural Crest Origin by Retinoic Acid and Wnt/β-Catenin Signaling," *Stem Cells Dev.*, 22(5): 828-839 (2013).
Inagaki et al., "Skin-Derived Precursors as a Source of Progenitors for Corneal Endothelial Regeneration," *Stem Cells Transl. Med.*, 6(3): 788-798 (2017).
Kinoshita et al., "Injection of Cultured Cells with a ROCK Inhibitor for Bullous Keratopathy," *New Engl. J. Med.*, 378(11): 995-1003 (2018).
Lee et al., "Derivation of neural crest cells from human pluripotent stem cells," *Nat. Protoc.*, 5(4): 688-701 (2010).
McCabe et al., "Efficient Generation of Human Embryonic Stem Cell-Derived Corneal Endothelial Cells by Directed Differentiation," *PLoS One*, 10(12): e0145266 (2015).
Okumura et al., "Rho kinase inhibitor enables cell-based therapy for corneal endothelial dysfunction," *Sci. Rep.*, 6: 26113 (2016).
Song et al., "Directed differentiation of human embryonic stem cells to corneal endothelial cell-like cells: A transcriptomic analysis," *Exp. Eye Res.*, 151: 107-114 (2016).
Zavala et al., "Corneal endothelium: developmental strategies for regeneration," *Eye (Lond.)*, 27(5): 579-588 (2013).
Zhang et al., "Isolation and Transplantation of Corneal Endothelial Cell-Like Cells Derived from In-Vitro-Differentiated Human Embryonic Stem Cells," *Stem Cells Dev.*, 23(12): 1340-1354 (2014).
Zhao et al., "Generation of Human Corneal Endothelial Cells via In Vitro Ocular Lineage Restriction of Pluripotent Stem Cells," *Invest. Ophthalmol. Vis. Sci.*, 57(15): 6878-6884 (2016).
Japanese Patent Office, International Search Report in International Patent Application No. PCT/JP2019/001142 (Apr. 16, 2019).
He et al., "3D Map of the Human Corneal Endothelial Cell," *Sci. Rep.*, 6: 29047 (2016).
Peh et al., "Cultivation of Human Corneal Endothelial Cells Isolated from Paired Donor Corneas" *PLoS One*, 6(12): e28310 (2011).
Schmitz et al., "Soluble Adenylyl Cyclase in Vascular Endothelium: Gene Expression Control of Epithelial Sodium Channel-α, $Na^+/K^+$-ATPase-α/β, and Mineralocorticoid Receptor," *Hypertension*, 63(4): 753-761 (2014).
Wagoner et al., "Feeder-free Differentiation of Cells Exhibiting Characteristics of Corneal Endothelium from Human Induced Pluripotent Stem Cells," *Biology Open*, 7(5): bio032102 (2018).

\* cited by examiner

Fig. 11
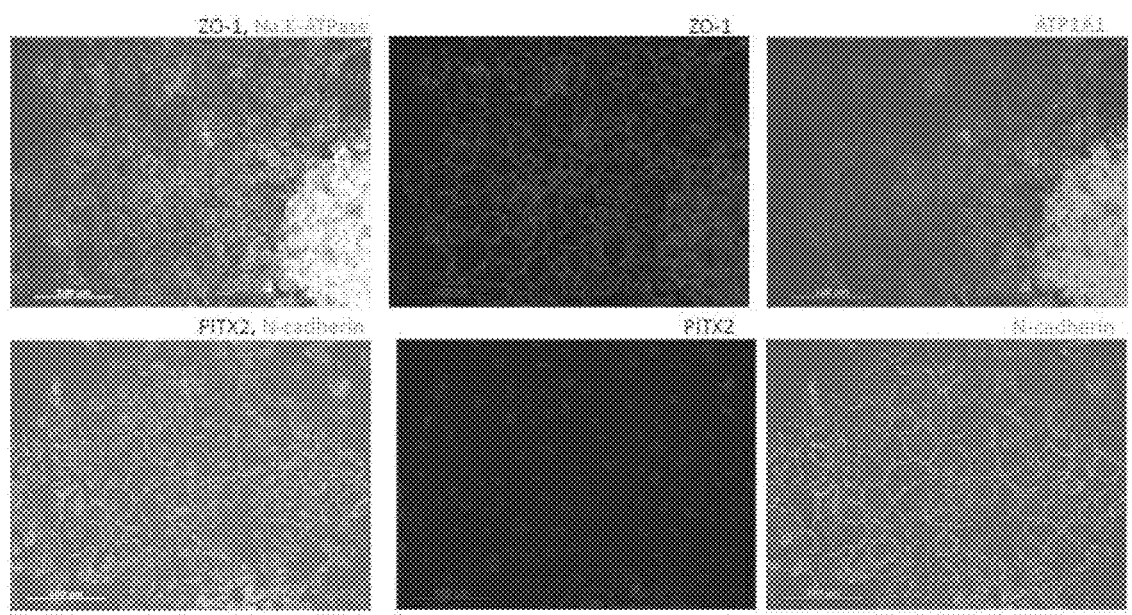
Fig. 12
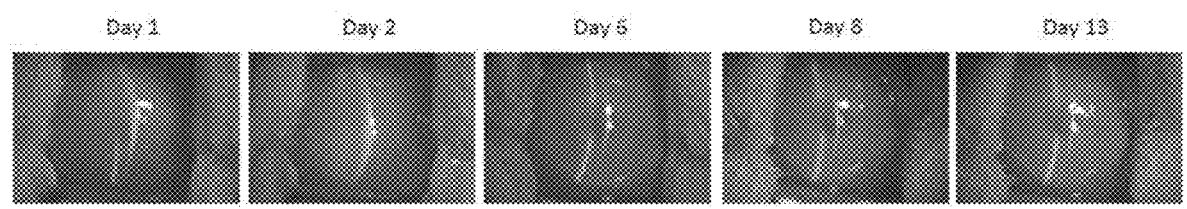
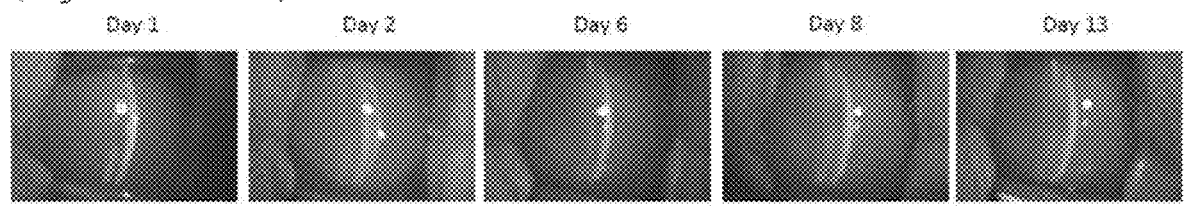

SEQUENCE LISTING

<160> NUMBER OF SEQ ID NOS: 28

<210> SEQ ID NO 1
<211> LENGTH: 20
<212> TYPE: DNA
<213> ORGANISM: Artificial Sequence
<220> FEATURE:
<223> OTHER INFORMATION: Synthetic Sequence - Forward Primer for OCT 4

<400> SEQUENCE: 1
gaaacccaca ctgcagcaga                    20

<210> SEQ ID NO 2
<211> LENGTH: 18
<212> TYPE: DNA
<213> ORGANISM: Artificial Sequence
<220> FEATURE:
<223> OTHER INFORMATION: Synthetic Sequence -Reverse Primer for OCT 4

<400> SEQUENCE: 2
tcgcttgccc ttctggcg                      18

<210> SEQ ID NO 3
<211> LENGTH: 21
<212> TYPE: DNA
<213> ORGANISM: Artificial Sequence
<220> FEATURE:
<223> OTHER INFORMATION: Synthetic Sequence - Forward Primer for KLF4

<400> SEQUENCE: 3
tgcggcaaaa cctacacaaa g                  21

<210> SEQ ID NO 4
<211> LENGTH: 20
<212> TYPE: DNA
<213> ORGANISM: Artificial Sequence
<220> FEATURE:
<223> OTHER INFORMATION: Synthetic Sequence - Reverse Primer for KLF4

<400> SEQUENCE: 4
gggcgaattt ccatccacag                    20

<210> SEQ ID NO 5
<211> LENGTH: 20

```
<212> TYPE: DNA
<213> ORGANISM: Artificial Sequence
<220> FEATURE:
<223> OTHER INFORMATION: Synthetic Sequence - Forward Primer for C-MYC

<400> SEQUENCE: 5
ggacccgctt ctctgaaagg                                            20

<210> SEQ ID NO 6
<211> LENGTH: 20
<212> TYPE: DNA
<213> ORGANISM: Artificial Sequence
<220> FEATURE:
<223> OTHER INFORMATION: Synthetic Sequence - Reverse Primer for C-MYC

<400> SEQUENCE: 6
taacgttgag gggcatcgtc                                            20

<210> SEQ ID NO 7
<211> LENGTH: 19
<212> TYPE: DNA
<213> ORGANISM: Artificial Sequence
<220> FEATURE:
<223> OTHER INFORMATION: Synthetic Sequence - Forward Primer for SOX2

<400> SEQUENCE: 7
gcgccctgca gtacaactc                                             19

<210> SEQ ID NO 8
<211> LENGTH: 19
<212> TYPE: DNA
<213> ORGANISM: Artificial Sequence
<220> FEATURE:
<223> OTHER INFORMATION: Synthetic Sequence - Reverse Primer for SOX2

<400> SEQUENCE: 8
cggacttgac caccgaacc                                             19

<210> SEQ ID NO 9
<211> LENGTH: 18
<212> TYPE: DNA
<213> ORGANISM: Artificial Sequence
<220> FEATURE:
<223> OTHER INFORMATION: Synthetic Sequence - Forward Primer for SOX9

<400> SEQUENCE: 9
aacgccttca tggtgtgg                                              18

<210> SEQ ID NO 10
<211> LENGTH: 21
<212> TYPE: DNA
<213> ORGANISM: Artificial Sequence
<220> FEATURE:
<223> OTHER INFORMATION: Synthetic Sequence - Reverse Primer for SOX9

<400> SEQUENCE: 10
tctcgctctc gttcagaagt c                                          21

<210> SEQ ID NO 11
<211> LENGTH: 19
<212> TYPE: DNA
<213> ORGANISM: Artificial Sequence
<220> FEATURE:
<223> OTHER INFORMATION: Synthetic Sequence - Forward Primer for LIN28A

<400> SEQUENCE: 11
```
tccgaaccaa cccttttgcc                                              19

<210> SEQ ID NO 12
<211> LENGTH: 20
<212> TYPE: DNA
<213> ORGANISM: Artificial Sequence
<220> FEATURE:
<223> OTHER INFORMATION: Synthetic Sequence - Reverse Primer for LIN28A

<400> SEQUENCE: 12
caaactgctg gttggacacg                                              20

<210> SEQ ID NO 13
<211> LENGTH: 21
<212> TYPE: DNA
<213> ORGANISM: Artificial Sequence
<220> FEATURE:
<223> OTHER INFORMATION: Synthetic Sequence - Forward Primer for PITX2

<400> SEQUENCE: 13
ctcctgagag ccgaaaagag g                                            21

<210> SEQ ID NO 14
<211> LENGTH: 21
<212> TYPE: DNA
<213> ORGANISM: Artificial Sequence
<220> FEATURE:
<223> OTHER INFORMATION: Synthetic Sequence - Reverse Primer for PITX2

<400> SEQUENCE: 14
attcttcccc tgctggcttt t                                            21

<210> SEQ ID NO 15
<211> LENGTH: 20
<212> TYPE: DNA
<213> ORGANISM: Artificial Sequence
<220> FEATURE:
<223> OTHER INFORMATION: Synthetic Sequence - Forward Primer for C-JUN

<400> SEQUENCE: 15
gagctggagc gcctgataat                                              20

<210> SEQ ID NO 16
<211> LENGTH: 20
<212> TYPE: DNA
<213> ORGANISM: Artificial Sequence
<220> FEATURE:
<223> OTHER INFORMATION: Synthetic Sequence - Reverse Primer for C-JUN

<400> SEQUENCE: 16
ccctcctgct catctgtcac                                              20

<210> SEQ ID NO 17
<211> LENGTH: 20
<212> TYPE: DNA
<213> ORGANISM: Artificial Sequence
<220> FEATURE:
<223> OTHER INFORMATION: Synthetic Sequence - Forward Primer for C-FOS

<400> SEQUENCE: 17
tactaccact cacccgcaga                                              20

<210> SEQ ID NO 18
<211> LENGTH: 20
<212> TYPE: DNA
<213> ORGANISM: Artificial Sequence

```
<220> FEATURE:
<223> OTHER INFORMATION: Synthetic Sequence - Reverse Primer for C-FOS

<400> SEQUENCE: 18
cgtgggaatg aagttggcac                                                   20

<210> SEQ ID NO 19
<211> LENGTH: 22
<212> TYPE: DNA
<213> ORGANISM: Artificial Sequence
<220> FEATURE:
<223> OTHER INFORMATION: Synthetic Sequence - Forward Primer for NR3C2

<400> SEQUENCE: 19
tgagctggag atcgtacaaa ca                                                22

<210> SEQ ID NO 20
<211> LENGTH: 20
<212> TYPE: DNA
<213> ORGANISM: Artificial Sequence
<220> FEATURE:
<223> OTHER INFORMATION: Synthetic Sequence - Reverse Primer for NR3C2

<400> SEQUENCE: 20
gtgcatcccc tggcatagtt                                                   20

<210> SEQ ID NO 21
<211> LENGTH: 20
<212> TYPE: DNA
<213> ORGANISM: Artificial Sequence
<220> FEATURE:
<223> OTHER INFORMATION: Synthetic Sequence - Forward Primer for SGK1

<400> SEQUENCE: 21
gcctgccgcc tttttatagc                                                   20

<210> SEQ ID NO 22
<211> LENGTH: 20
<212> TYPE: DNA
<213> ORGANISM: Artificial Sequence
<220> FEATURE:
<223> OTHER INFORMATION: Synthetic Sequence - Reverse Primer for SGK1

<400> SEQUENCE: 22
caggaggtgt cttgcggaat                                                   20

<210> SEQ ID NO 23
<211> LENGTH: 20
<212> TYPE: DNA
<213> ORGANISM: Artificial Sequence
<220> FEATURE:
<223> OTHER INFORMATION: Synthetic Sequence - Forward Primer for ATP1A1

<400> SEQUENCE: 23
ccaaagacag ggtgctatcg                                                   20

<210> SEQ ID NO 24
<211> LENGTH: 20
<212> TYPE: DNA
<213> ORGANISM: Artificial Sequence
<220> FEATURE:
<223> OTHER INFORMATION: Synthetic Sequence - Reverse Primer for ATP1A1

<400> SEQUENCE: 24
ttgcttggac acatctgagc                                                   20
```

-continued

```
<210> SEQ ID NO 25
<211> LENGTH: 20
<212> TYPE: DNA
<213> ORGANISM: Artificial Sequence
<220> FEATURE:
<223> OTHER INFORMATION: Synthetic Sequence - Forward Primer for ITGA3

<400> SEQUENCE: 25
ggtgcctaca actggaaagg                                                 20

<210> SEQ ID NO 26
<211> LENGTH: 20
<212> TYPE: DNA
<213> ORGANISM: Artificial Sequence
<220> FEATURE:
<223> OTHER INFORMATION: Synthetic Sequence - Reverse Primer for ITGA3

<400> SEQUENCE: 26
gcctacctgc atcgtgtacc                                                 20

<210> SEQ ID NO 27
<211> LENGTH: 20
<212> TYPE: DNA
<213> ORGANISM: Artificial Sequence
<220> FEATURE:
<223> OTHER INFORMATION: Synthetic Sequence - Forward Primer for ADRB2

<400> SEQUENCE: 27
ttttggcaac ttctggtgcg                                                 20

<210> SEQ ID NO 28
<211> LENGTH: 20
<212> TYPE: DNA
<213> ORGANISM: Artificial Sequence
<220> FEATURE:
<223> OTHER INFORMATION: Synthetic Sequence - Reverse Primer for ADRB2

<400> SEQUENCE: 28
gatcacgcac agggtctcaa                                                 20
```

MEDIUM COMPRISING SERUM REPLACEMENT, IGF1, STAT3 ACTIVATOR AND ADRENAL GLAND HORMONE WITHOUT BFGF OR ROCK INHIBITOR FOR PRODUCING CORNEAL ENDOTHELIAL SUBSTITUTE CELLS FROM iPS CELLS AND A METHOD THEREOF

CROSS-REFERENCE TO RELATED APPLICATIONS

This patent application is the U.S. national phase of International Patent Application No. PCT/JP2019/001142, filed on Jan. 16, 2019, which claims the benefit of Japanese Patent Application No. 2018-005076 filed on Jan. 16, 2018, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 6,391 bytes ASCII (Text) file named "750242SequenceListing.txt," Jul. 16, 2020.

TECHNICAL FIELD

The present invention relates to a method for inducing a corneal endothelial substitute cell from an iPS cell. Furthermore, the present invention relates to a corneal endothelial substitute cell obtained by the method, a medicament using the same and the like.

BACKGROUND ART

The above-mentioned function of corneal endothelial cell is impaired by a damage to the corneal endothelium such as a decrease in the corneal endothelial cell and the like, thus resulting in the edema of the corneal stroma. This decreases transparency of the cornea, and reduces the visual acuity. Such condition is called bullous keratopathy. In the meantime, it is known that human corneal endothelial cell once injured scarcely shows an ability to regenerate. When the corneal endothelial cells have decreased due to certain injury, an effective and sole treatment thereof is corneal transplantation. In fact, about half the number of applicable cases of corneal transplantation is for bullous keratopathy caused by corneal endothelial functional disorder.

At present, patients with corneal endothelium damage are treated by penetrating keratoplasty wherein the whole three-layer structure of corneal epithelium, corneal stroma and corneal endothelium is transplanted. While the penetrating keratoplasty is an established technique, the supply of cornea is short in Japan as the situation stands, and the rejection reaction poses a problem. To solve such problems, "part transplantation" involving transplantation of only the damaged tissue is becoming popular. Deep lamellar keratoplasty (DLKP) involving transplantation of only the epithelium and stroma of the donor while preserving corneal endothelium, corneal endothelium transplantation involving transplantation of only the part cornea including endothelium and the like are known. However, in the case of corneal endothelium transplantation, for example, the source of supply of the material for transplantation is still the corneal endothelium itself. Since the number of donor of cornea is limited, the problem of donor shortage cannot be overcome, like penetrating keratoplasty. Furthermore, since corneal endothelial cell is difficult to culture, preparation of cultured cells in a number sufficient for transplantation places a large burden in terms of time and cost.

To solve the problem of lack of donors, attempts have been made to create corneal endothelial cells or cells that have a function equivalent to that of corneal endothelial cells and that substitute for corneal endothelial cells.

As a method for inducing corneal endothelial cell (actually cells with properties similar to those of corneal endothelial cells since expression of surface markers specific to corneal endothelial cells has not been confirmed) from iPS cell, an induction method using bovine serum, Matrigel, HE-SFM (component unknown) in the basal medium has been reported (non-patent document 1). As an induction method from ES cells, a method using bovine serum and Conditioned medium for bovine corneal endothelial cells (non-patent document 2), and an induction method using bovine serum, bovine pituitary gland extract and the like (non-patent document 3) have been reported.

However, the mechanism of induction from stem cells to the corneal endothelium has not been elucidated because both rely on additives made of animal-derived components such as bovine serum. In addition, they are not production methods of a level that can be used in clinical researches since they use biological materials. These methods are performed by inducing neural crest cells from iPS cells/ES cells and then inducing corneal endothelial cells from the neural crest cells.

The present inventors have previously found and reported a method for producing a cell having functions equivalent to those of a corneal endothelial cell, and capable of substituting for the corneal endothelial cell (patent document 1). However, this method is also a method for inducing corneal endothelial cells from iPS cells through neural crest cells.

DOCUMENT LIST

Patent Document patent document 1: JP-B-6041270

Non-Patent Documents non-patent document 1: Invest Ophthalmol Vis Sci. 2016 Dec. 1; 57(15):6878-6884.
non-patent document 2: Exp Eye Res. 2016 October; 151: 107-14.
non-patent document 3: PLoS One. 2015 Dec. 21; 10(12): e0145266.

SUMMARY OF INVENTION

Technical Problem

To process target cells derived from iPS cells or ES cells into final products through clinical researches or clinical trials, it is desirable that the production process be as simple and efficient as possible, that the starting materials used in the production process be chemically defined, and that no animal-derived components be included. Needless to say, it is more preferable that the mechanism of induction into target cells is known, based on which an evaluation method to check that the induction proceeds well during the production process is established.

At present, a cell derived from iPS cell or ES cell and established with a surface marker specific for corneal endothelial cell does not exist. Therefore, no matter how much the cell resembles a corneal endothelial cell, it is not possible to prove that the cell is a corneal endothelial cell itself. Therefore, the present inventors refer to a cell having functions equivalent to those of corneal endothelial cell as a corneal endothelial substitute cell, particularly, they refer to a corneal endothelial substitute cell induced from an iPS cell as a corneal endothelial cell substitute from iPS cells (CECSi cell), and have tried to establish a method for efficiently producing the CECSi cell.

In the prior art, induction of a corneal endothelial substitute cell from iPS cell or ES cell requires once inducing to a neural crest cell, which problematically renders the work process complicated. In the induction methods by the past reports, as mentioned above, the mechanism of induction from stem cells to corneal endothelial substitute cells has not been elucidated because they rely on additives made of animal-derived components such as bovine serum. In addition, the methods are not production methods of a level that can be used in clinical researches since they use biological materials.

Therefore, the present invention aims to (1) provide new corneal endothelium regenerative medicine in which CECSi cells are directly induced without going through a step of inducing iPS cells into neural crest cells, and are used to treat diseases such as bullous keratopathy that require transplantation of corneal endothelial cells, and (2) in the production process of CECSi cells, the scaffold material and the medium components used for the induction of the cells provide a completely xeno-free and chemically defined environment. Furthermore, the present invention aims to provide an evaluation method capable of confirming whether or not CECSi cells are successfully induced, and the induction efficiency during the production process.

Solution to Problem

In view of the above-mentioned problems, the present inventors have conducted intensive studies and found that iPS cells can be directly and efficiently induced to differentiate into CECSi cells by adhesive culture of iPS cells in a medium containing a particular differentiation inducing factor, without an induction step into neural crest cells, which resulted in the completion of the present invention.

Therefore, the present invention provides the following.

[1] A medium for inducing a cornea endothelial substitute cell from an iPS cell, the medium comprising an insulin-like growth factor and a STAT3 activator, and not comprising a basic fibroblast growth factor or a ROCK inhibitor.

[2] The medium of the above-mentioned [1], wherein the insulin-like growth factor is IGF1.

[3] The medium of the above-mentioned [1] or [2], wherein the STAT3 activator is LIF and/or IL-6.

[4] The medium of any of the above-mentioned [1] to [3], further comprising a keratinocyte growth factor.

[5] The medium of any of the above-mentioned [1] to [4], further comprising TGF-beta 1.

[6] The medium of any of the above-mentioned [1] to [5], further comprising adrenal gland hormone.

[7] The medium of the above-mentioned [6], wherein the adrenal gland hormone is corticosteroid.

[8] The medium of the above-mentioned [7], wherein the corticosteroid is mineralocorticoid and/or glucocorticoid.

[9] The medium of the above-mentioned [8], wherein the mineralocorticoid is aldosterone.

[10] The medium of the above-mentioned [8], wherein the glucocorticoid is dexamethasone and/or hydrocortisone.

[11] The medium of any of the above-mentioned [1] to [10], further comprising ascorbic acid.

[12] A method for producing a corneal endothelial substitute cell from an iPS cell, the method comprising adhesion-culturing in a medium comprising an insulin-like growth factor and a STAT3 activator, and not comprising a basic fibroblast growth factor or a ROCK inhibitor.

[13] The method of the above-mentioned [12], wherein the insulin-like growth factor is IGF1.

[14] The method of the above-mentioned [12], wherein the STAT3 activator is LIF and/or IL-6.

[15] The method of any of the above-mentioned [12] to [14], further comprising a keratinocyte growth factor.

[16] The method of any of the above-mentioned [12] to [15], wherein the medium further comprises TGF-beta 1.

[17] The method of any of the above-mentioned [12] to [16], wherein the medium further comprises adrenal gland hormone.

[18] The method of the above-mentioned [17], wherein the adrenal gland hormone is corticosteroid.

[19] The method of the above-mentioned [18], wherein the corticosteroid is mineralocorticoid and/or glucocorticoid.

[20] The method of the above-mentioned [19], wherein the mineralocorticoid is aldosterone.

[21] The method of the above-mentioned [19], wherein the glucocorticoid is dexamethasone and/or hydrocortisone.

[22] The method of any of the above-mentioned [12] to [21], further comprising ascorbic acid.

[23] A method for producing a corneal endothelial substitute cell from an iPS cell, the method comprising adhesion-culturing in the medium of any of the above-mentioned [1] to [11].

[24] A cell capable of substituting for a corneal endothelial cell, wherein the cell has property and function like those of a corneal endothelial cell and shows an enhanced gene expression level of NR3C2 (nuclear receptor subfamily 3, group C, member 2).

[25] The cell of the above-mentioned [24], wherein the property and function like those of a corneal endothelial cell satisfy one or more of the following requirements:
(i) intercellular adhesion is constituted of N-cadherin,
(ii) intercellular tight junction is formed,
(iii) Na,K-ATPase α1 subunit is expressed on a cellular membrane,
(iv) expression of transcription factor PITX2 is observed in the cell nucleus.

[26] The cell of the above-mentioned [24] or [25] produced by the method of any of the above-mentioned [12] to [23].

[27] The cell of any of the above-mentioned [24] to [26], wherein a gene expression level of NR3C2 is not less than an expression level of B4G12 cell of the corneal endothelial cell line.

[28] A medicament comprising the corneal endothelial substitute cell of any of the above-mentioned [24] to [27].

[29] The medicament of the above-mentioned [28] for use for transplantation.

Advantageous Effects of Invention

According to the production method of the present invention, a corneal endothelial substitute cell can be produced more efficiently and safely from an iPS cell. The corneal endothelial substitute cell obtained by the production method can be used as a medicament for the treatment of a disease caused by functional disorder of corneal endothelial cell, such as a corneal sheet for corneal transplantation and the like, or for cellular therapy for treating such disease.

BRIEF DESCRIPTION OF DRAWINGS

FIG. 11: a cryopreserved cell stock was thawed, spheroids were formed, and then adherent culture was performed in a culture dish. FIG. 11 is a micrograph showing the examination results of the expression of ZO-1, ATP1A1, PITX2, and N-cadherin on day 2 after seeding. The spheroid maintained the expression of ZO-1, ATP1A1, PITX2 and N-cadherin, and was able to migrate while maintaining the quality.

FIG. 12 is a photograph showing the results of corneal transparency recovery in an experiment of CECSi cell spheroid transplantation onto the posterior surface of a rabbit cornea. The edema opacity of the cornea was improved and the transparency was recovered in the CECSi cell transplantion group.

DESCRIPTION OF EMBODIMENTS

Figure 1:
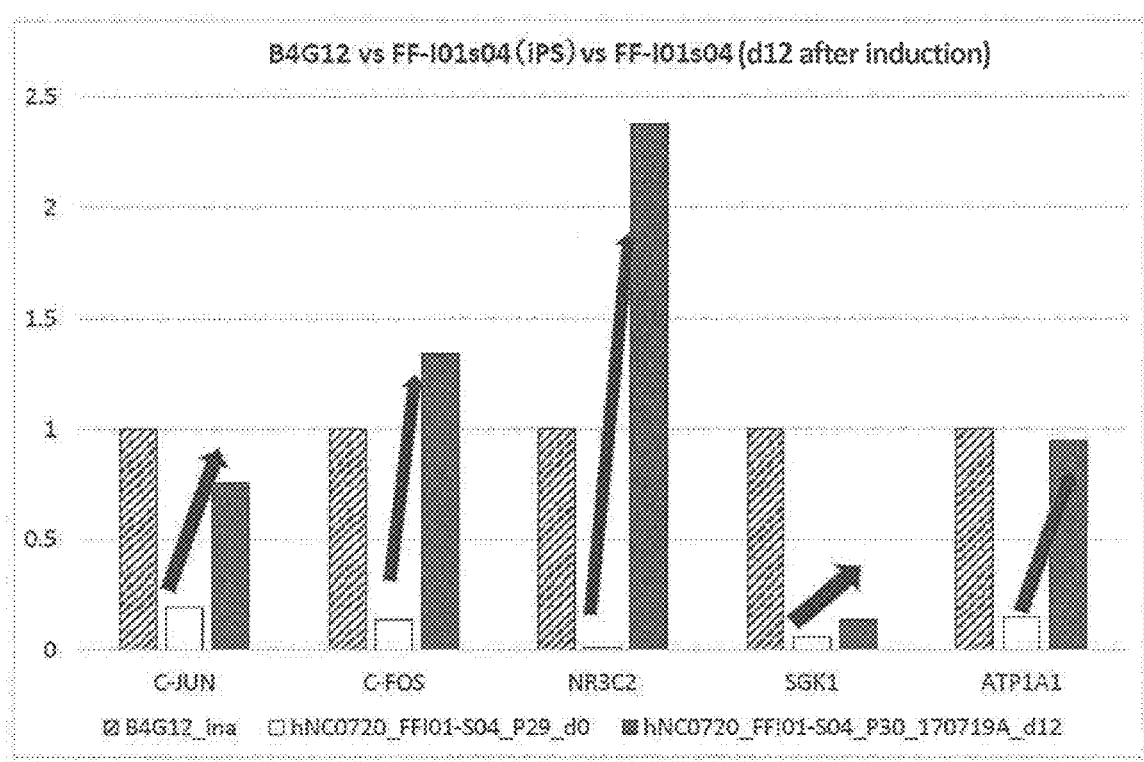
FIG. 1 shows changes in the gene expression in induction of differentiation into CECSi cells. Respective bars show, from the left, the results of B4G12 cells (corneal endothelial cell line) (B4G12_ina), FF-I01s04 line (iPS cell) (hNC0720_FFI01-S04_P29_d0) before induction, and FF-I01s04 line (iPS cell) (hNC0720_FFI01-S04_P30_170719A_d12) on day 12 from the differentiation induction. An increase in the expression of marker gene of the corneal endothelial cell was confirmed along with the differentiation induction.

The present invention is explained in the following. Unless particularly indicated, the terms used in the present specification have the meanings generally used in the pertinent field.

The present invention is characterized by the use of an iPS cell as a stem cell to be the source of corneal endothelial substitute cells. The stem cell refers to a cell capable of being cultured in vitro, and capable of differentiating into plural lines of cells constituting the body. Specific examples include embryonic stem cell (ES cell), embryonic primordial germ cell-derived pluripotent stem cell (EG cell), testis-derived pluripotent stem cell (GS cell), somatic cell-derived induced pluripotent stem cell (iPS cell), and human somatic stem cell (tissue stem cell). As the iPS cell, an iPS cell derived from any warm-blooded animal, preferably a mammal, can be used. Examples of the mammal include mouse, rat, guinea pig, hamster, rabbit, cat, dog, sheep, swine, bovine, horse, goat, monkey, human and the like. A cell derived from human can be preferably used.

Specific examples of the iPS cell include cells obtained by introducing plural genes into a somatic cell such as skin cell and the like, which have acquired multipotency same as that of ES cell. Examples thereof include iPS cell obtained by introducing Oct3/4 gene, Klf4 gene, C-Myc gene and Sox2 gene, iPS cell obtained by introducing Oct3/4 gene, Klf4 gene and Sox2 gene (Nat Biotechnol 2008; 26: 101-106) and the like. Furthermore, the production method of iPS cell has been intensively improved technically, for example, a method involving further reducing transgenes (Nature. 2008 Jul. 31; 454(7204): 646-50), a method utilizing a low-molecular-weight compound (Cell Stem Cell. 2009 Jan. 9; 4(1): 16-9, Cell Stem Cell. 2009 Nov. 6; 5(5): 491-503), a method utilizing a transcription factor protein instead of the gene (Cell Stem Cell. 2009 May 8; 4(5): 381-4) and the like. Since the basic property of the iPS cells produced, that is, having multipotency, is equivalent irrespective of the production methods, all of them can be used as the method of the present invention.

To be specific, as iPS cell, 201B7, 201B7-Ff, 253G1, 253G4, 1201C1, 1205D1, 1210B2, 836B3, FF-I14s03, FF-I01s04, MH09s01 (all iPS Academia Japan or the Center for iPS Cell Research and Application, Kyoto University), Tic (JCRB1331 line), Dotcom (JCRB1327 line), Squeaky (JCRB1329 line), and Toe (JCRB1338 line), Lollipop (JCRB1336 line) (above, National Center for Child Health and Development, National Institute of Biomedical Innovation, JCRB Cell Bank), UTA-1 line and UTA-1-SF-2-2 line (both the University of Tokyo) and the like can be used.

1. Production Method of Cell (Method for Induction of Cell Differentiation)

The present invention provides a method for producing a corneal endothelial substitute cell from an iPS cell, that is, a method for producing an iPS cell-derived corneal endothelial substitute cell (CECSi cell) (hereinafter to be also referred to as the production method of the present invention). The method is also a method for inducing differentiation of a cell in a more undifferentiated state into a cell in a more differentiated state.

The present invention provides a method for producing a corneal endothelial substitute cell, including a step of culturing iPS cells in a medium containing an insulin-like growth factor and a STAT3 activator and not containing a basic fibroblast growth factor or a ROCK inhibitor, and used for inducing differentiation of iPS cell into CECSi cell (hereinafter to be also referred to as the differentiation induction medium of the present invention).

The iPS cell to be used in this step is as mentioned above. It is preferably FF-I01s04 and QHJI01s04 which is a clinical cell line of the same clone as FF-I01s04, or FF-I14s03 and QHJI14s03 which is a clinical cell line of the same clone as FF-I14s03.

The production method and differentiation induction medium of the present invention are characterized by the use of a compound that activates an insulin-like growth factor and STAT3.

Insulin-like growth factor (IGF) is a polypeptide having a sequence highly similar to that of insulin and is known to be related to cell proliferation and differentiation. IGF has been clarified to include two molecular species called IGF1 and IGF2, respectively. IGF1 and IGF2 are respectively composed of 70 (molecular weight 7649) and 67 (molecular weight 7471) amino acids. Both are known to promote cell proliferation in cultured cell lines, and in the body, production and secretion of IGF1 are regulated in response to growth hormone, insulin, or nutritional status, and those of IGF2 are regulated in response to the development of tissue.

While IGF to be used in the present invention may be IGF1 or IGF2 as long as the effect of inducing differentiation of iPS cell into CECSi cell is afforded, it is preferably IGF1. IGF, IGF1, and IGF2 are commercially available or can be prepared according to known sequence and known documents of the polypeptide. The concentration of IGF in the medium is generally 2-500 ng/mL, preferably 10-100 ng/mL, more preferably about 20 ng/mL.

For IGF, a fragment or variant thereof can be used as long as the desired activity (effect contributing to induction of differentiation into CECSi cells) is maintained.

Compounds that activate STAT3 increase expression of the below-mentioned adrenal gland hormone, particularly mineralocorticoid receptor, whereby differentiation into CECSi cell is promoted.

STAT3 is one kind of STAT (signal transducer and activator of transcription) protein (STATs 1, 2, 3, 4, 5a, 5b and 6 are known for mammals) and, like other STAT family proteins, is a transcription factor involved in intracellular signal transduction (e.g., JAK-STAT pathway) of cytokine, hormone, growth factor and the like. The compounds that activate STAT3 (hereinafter to be also referred to as STAT3 activator) include interleukin-6 (IL-6), leukemia inhibitory factor (LIF), oncostatin M, leptin, epithelial growth factors (EGF) and the like. They are preferably compounds belonging to the IL-6 family, that is, ligands capable of binding to the IL-6 receptor family and gp130, more preferably IL-6 and LIF. The STAT3 activator is commercially available, or can also be prepared by reference to known documents. While the concentration of the STAT3 activator in the medium varies depending on the kind of the compound to be used, in the case of LIF or IL-6, it is generally 0.1-50 ng/mL, preferably 0.5-10 ng/mL, more preferably about 2 ng/mL. One or 2 or more kinds of the STAT3 activator may be used, in which case the concentration of each compound in the medium is appropriately adjusted.

Furthermore, the production method and differentiation induction medium of the present invention are characterized in that they do not use a basic fibroblast growth factor (bFGF) or a ROCK (Rho-associated, coiled-coil-containing kinase) inhibitor. bFGF and ROCK inhibitors are commonly used to induce differentiation of stem cells. As shown in the below-mentioned Example, it was found in the present invention that these factors are unfavorable for the induction of differentiation of iPS cells into CECSi cells.

In the production method and differentiation induction medium of the present invention, it is preferable to further use a keratinocyte growth factor.

The keratinocyte growth factor (KGF) is one kind of the fibroblast growth factor (FGF) family, and is also known as FGF-7. It is a glycoprotein consisting of 194 amino acid residues and with a molecular weight of about 27,000, and is a growth factor that promotes the growth of epithelial and epidermal cells. KGF is commercially available or can be prepared according to known sequence and known documents of the protein. The concentration of KGF in the medium is generally 0.5-20 ng/mL, preferably 2-10 ng/mL, more preferably about 5 ng/mL.

The production method and differentiation induction medium of the present invention preferably further use transforming growth factor beta 1 (TGF-beta 1). By adding TGF-beta 1 to the medium, the expression of N-cadherin can be maintained and the cell morphology can be maintained even when the number of passages of cells is advanced.

TGF-beta 1 is one of the three kinds of isoform (beta 1, beta 2, beta 3) of transforming growth factor beta (TGF-beta), and is a protein having an action of suppression of cell proliferation, production of extracellular matrix, suppression of immunocompetence and the like. TGF-beta 1 is commercially available, or can be prepared by reference to known sequences and known documents. The concentration of TGF-beta 1 in the medium is generally 0.05-20 ng/mL, preferably 0.5-10 ng/mL, more preferably about 1 ng/mL.

The production method and differentiation induction medium of the present invention preferably further use an adrenal gland hormone. The adrenal gland hormones are involved in increased expression of $Na^+,K^+$-ATPase, which is an index of being able to function as a corneal endothelial cell. Adrenal gland hormones are hormones that are synthesized and secreted by the adrenal gland, and catecholamine is secreted from the medulla and corticosteroid such as glucocorticoid, mineralocorticoid and the like, and adrenal sex hormone are secreted from the cortex. In the present invention, the adrenal gland hormone is preferably corticosteroid. These hormones may be synthetic substances as long as they have the same action. Corticosteroid is divided into glucocorticoid and mineralocorticoid. As the glucocorticoid, dexamethasone, hydrocortisone, betamethasone, beclomethasone and the like can be mentioned. Among these, dexamethasone and hydrocortisone are preferably used. As the mineralocorticoid, aldosterone, dehydroepiandrosterone, androstenedione and the like can be mentioned. Among these, aldosterone is preferable. Adrenal gland hormone is commercially available, or can be prepared according to known documents. The concentration of the adrenal gland hormone in the medium varies depending on the kind of the compound to be used. When the compound is corticosteroid such as dexamethasone or the like, it is generally 3.8-3,800 ng/mL, preferably 7.6-380 ng/mL, more preferably about 38 ng/mL. When the compound is mineralocorticoid such as aldosterone or the like, it is generally 50-5,000 ng/mL, preferably 100-1,000 ng/mL, more preferably about 720 ng/mL. One or 2 or more kinds of the adrenal gland hormone may be used, and are preferably used in combination. In this case, the concentration of each compound in the medium is appropriately adjusted.

Like adrenal gland hormone, catecholamines may also be used as a factor involved in increased expression of $Na^+$, $K^+$-ATPase. As the catecholamines, for example, adrenaline, noradrenaline, dopamine and the like can be mentioned. The concentration of catecholamine in the medium varies depending on the kind of the compound to be used. When catecholamine is adrenaline, it is generally 0.1-10 µg/mL, preferably 0.2-1 µg/mL, more preferably about 0.5 µg/mL. One or 2 or more kinds of catecholamine may be used, in which case the concentration of each compound in the medium is appropriately adjusted.

The above-mentioned IGF and STAT3 activator and, when desired, KGF, TGF-beta 1, and adrenal gland hormone are generically referred to as the differentiation inducing factor of the present invention. In the present invention, at least two kinds of IGF and STAT3 activator are contained in a differentiation induction medium. Preferably, at least one kind, preferably two kinds, more preferably three kinds, selected from KGF, TGF-beta 1, and adrenal gland hormone (preferably corticosteroid), further preferably all four kinds thereof, are contained in the differentiation induction medium of the present invention.

In this step, respective differentiation inducing factors may be simultaneously added to a medium, or may be separately added to a medium in a staggered manner as long as differentiation of iPS cell into CECSi cell can be induced. It is convenient and preferable to simultaneously add each differentiation inducing factor to a medium.

The medium to be used in this step is not particularly limited as long as it contains each differentiation inducing factor as mentioned above, and is generally a medium used for cultivating iPS cells (hereinafter to be also referred to as a basal medium for convenience) and added with each differentiation inducing factor. The basal medium is not particularly limited as long as it can be used for culturing animal cells, and includes, for example, MEM medium, BME medium, BGJb medium, CMRL 1066 medium, Glasgow MEM medium, Improved MEM Zinc Option medium, IMDM medium, Medium 199 medium, Eagle MEM medium, ° MEM medium, DMEM medium, ham medium (e.g., F10, F12), RPMI 1640 medium, Fischer's medium, and a mixed medium thereof. These media are commercially available. Furthermore, the medium to be used in the present invention may be a serum-containing medium or serum-free medium. It is preferably a serum-free medium. When the medium to be used in the present invention is a serum-containing medium, mammalian sera such as bovine serum, fetal bovine serum and the like can be used. The concentration of the serum in a medium is 0.1-20%, preferably 1-10%.

The basal medium to be used in the present invention is preferably a DMEM/F12 medium which is a mixed medium of DMEM medium and Ham's F12 medium.

The medium to be used in the present invention may also contain a serum replacement. Examples of the serum replacement include albumin (e.g., lipid rich albumin), transferrin, fatty acid, collagen precursor, antioxidant (e.g., ascorbic acid and the like), trace element (e.g., zinc, selenium, etc.), B-27 supplement, N2 supplement, knockout serum replacement, 2-mercaptoethanol or 3'thiolglycerol, equivalents thereof and the like. These serum replacements are also commercially available. Where necessary, the medium can contain vitamin, buffering agent, inorganic salts, antibiotic (e.g., penicillin, streptomycin) and the like.

One preferred embodiment of the differentiation induction medium to be used in this step is a medium having the composition shown in the following Table.

TABLE 1

| (basal medium: DMEM/F12) |
|---|
| components |
| N2 max supplement |
| KGF |
| IGF1 |
| TGF beta 1 |
| LIF |
| KGF |
| IL6 |
| adrenaline |
| dexamethasone |
| aldosterone |
| ascorbic acid |

The step of inducing differentiation of iPS cells into CECSi cells in the production method of the present invention is performed by culturing in a $CO_2$ incubator aerated with 1-10%, preferably 5%, carbon dioxide at a culture temperature suitable for culture of iPS cells to be used, generally 30-40° C., preferably about 37° C., in the differentiation induction medium of the present invention for a period sufficient for inducing differentiation into CECSi cells. The culture period is generally 10 to 40 days, preferably 10 to 28 days, after the start of induction. Where necessary, the medium is exchanged as appropriate (e.g., once every 3 days). Where necessary, the first passage is performed during 11 to 15 days after the start of induction. In addition, where necessary, the second passage is performed during 3 to 10 days after the first passage.

In the production method of the present invention (differentiation induction method), iPS cells are generally adhesive cultured on a culture vessel. The culture vessel used here includes, for example, flask, tissue culture flask, dish, petri dish, tissue culture dish, multiple dish, microplate, microwell plate, multiplate, multiwell plate, chamber slide, schale, tube, tray, culture bag, and roller bottle. It is preferably dish, petri dish, tissue culture dish, multiple dish, microplate, microwell plate, multiplate, multiwell plate or the like. The culture vessel preferably has a coating suitable for maintaining and culturing stem cells. Specifically, it is preferable to use feeder cells or a culture vessel coated with an extracellular matrix component. The feeder cell is not particularly limited and includes, for example, fibroblast (mouse embryonic fibroblast (MEF), mouse fibroblast (STO) etc.). The feeder cell is preferably inactivated by a method known per se, for example, radiation (gamma ray etc.), anticancer agent (mitomycin C etc.) treatment and the like. Examples of the extracellular matrix component include fibrous proteins such as gelatin, collagen, elastin and the like, glucosaminoglycan and proteoglycan such as hyaluronic acid, chondroitin sulfate and the like, cell adhesive proteins such as fibronectin, vitronectin, laminin and the like, basement membrane components such as Matrigel and the like, and the like. Preferred coating base material includes laminin 511-E8 fragment (e.g., iMatrix, Nippi) which is an enzymatic degradation fragment of laminin 511.

In the present invention, induction of differentiation of iPS cells into CECSi cells can be confirmed by evaluating the presence or absence of the expression of a protein for exhibiting the corneal endothelial cell-like properties and functions, or a gene encoding the protein (corneal endothelial cell marker). The expression of the protein can be evaluated by a method utilizing an antigen antibody reaction and the like, and the expression of the gene can be evaluated by a method utilizing RT-PCR and the like. Examples of the marker include proteins related to pump function and barrier function of corneal endothelial cells and genes encoding the same, such as ZO-1, N-cadherin, $Na^+,K^+$-ATPase (particularly $\alpha 1$ subunit), $Na^+,HCO_3$-co-transporter, collagen type IV, collagen type VIII, carbonic anhydrase, Keratin 8, Keratin 18, Paired-like homeodomain transcription factor 2 (PITX2), Integrin alpha 3, Claudin 10b and the like. It can also be confirmed by observing the expression of the transcription factor PITX2 in the cell nucleus.

As shown in the Example of the present specification, CECSi cell is characterized in that the gene expression level of NR3C2 (nuclear receptor subfamily 3, group C, member 2) is enhanced. Specifically, the expression level thereof is not less than that in B4G12 cells (corneal endothelial cell line). Therefore, the differentiation induction of iPS cells into CECSi cells can also be confirmed by evaluating the degree of increase in the NR3C2 expression level. B4G12 cell is a cell line established from a cell obtained by transforming a cell which was derived from the normal cell of the post-corneal epithelium of a 91-year-old Caucasian female with the early region of the SV40 genome, and can be obtained from a German cell bank (German Collection of Microorganisms and Cell Cultures GmbH) and the like.

In addition, confirmation that the iPS cell has been induced to differentiate into CECSi cell can be evaluated by measuring the $Na^+,K^+$-ATPase pumping function of the cell. The $Na^+,K^+$-ATPase pumping function of the cell can be measured, for example, according to the methods described in Investigative Ophthalmology & Visual Science, 2010 vol. 51, No. 8, 3935-3942, and Current Eye Research, 2009 vol. 34, 347-354 and using the Ussing chamber.

Conveniently, differentiation induction can also be confirmed by evaluating the cell morphology. A cell differentiated into an endothelial cell shows a mosaic growth form, and further, a tight junction is formed in the cell.

In the production method of the present invention, CECSi cells can be supplied in large amounts by efficiently inducing iPS cells to differentiate into CECSi cells. The obtained CECSi cells can be utilized as a medicament such as a corneal endothelial cell sheet for corneal transplantation and the like.

2. Corneal Endothelial Substitute Cell (CECSi Cell)

The present invention provides a CECSi cell, preferably a CECSi cell produced by the above-mentioned production method of the present invention (sometimes to be abbreviated as the cell of the present invention in the present specification).

The cell of the present invention is characterized in that it has property and function like those of a corneal endothelial cell and capable of substituting for a corneal endothelial cell, wherein a gene expression level of NR3C2 (nuclear receptor subfamily 3, group C, member 2) is enhanced.

NR3C2 is a mineralocorticoid receptor that controls the expression level of Na,K-ATPase. In the cell of the present invention, the gene expression level of the receptor is enhanced. Specifically, the expression level thereof is not less than that in B4G12 cells known as a corneal endothelial cell line. The gene expression level of NR3C2 can be measured and evaluated by quantitative PCR and the like.

As the corneal endothelial cell-like property and function, the following characteristics (i) to (iv) can be specifically mentioned, and at least one, preferably two, more preferably three, further preferably all four, of these characteristics are shown.

(i) intercellular adhesion is constituted of N-cadherin,
(ii) intercellular tight junction is formed,
(iii) Na,K-ATPase $\alpha 1$ subunit is expressed on a cellular membrane,
(iv) expression of transcription factor PITX2 is observed in the cell nucleus.

Whether intercellular adhesion is constituted of N-Cadherin can be confirmed by immunostaining for N-Cadherin.

Whether an intercellular tight junction is formed can be confirmed by observing the presence of ZO-1 which is a protein constituting the tight junction by immunostaining for ZO-1. It can also be confirmed by directly observing the structure with an electron microscope.

Whether the Na,K-ATPase $\alpha 1$ subunit (ATP1A1) is expressed on a cellular membrane can be confirmed when the both are co-stained in immunostaining for ZO-1 and Na,K-ATPase $\alpha 1$ subunit.

Whether the transcription factor PITX2 is expressed in the cell nucleus can be confirmed by immunostaining for PITX2.

More specifically, each characteristic can be confirmed by the method described in the Example.

3. Medicament Containing Cells

The present invention provides a medicament containing CECSi cells, preferably CECSi cells produced by the above-mentioned production method of the present invention (sometimes to be abbreviated in the present specification as the medicament of the present invention).

When a medicament containing CECSi cells is produced as a cell sheet, iPS cells are plated on a culture substrate, and cultured in the differentiation induction medium of the present invention to induce differentiation into CECSi cells on the culture substrate. While the culture substrate to be used in the present invention is not particularly limited as long as it is for cell culture, for example, naturally-occurring substance-derived polymer materials such as collagen, gelatin, cellulose, laminin and the like, synthetic polymer materials such as polystyrene, polyester, polycarbonate, poly(N-isopropylacrylamide) and the like, biodegradable polymer materials such as polylactic acid, polyglycolic acid and the like, hydroxyapatite, amniotic membrane and the like can be mentioned. Preferably, a culture substrate that does not cause rejection during transplantation is appropriately used according to the transplantation subject.

For transplantation, confluent CECSi cells are used. For this end, the number of iPS cells is generally set such that the cells are seeded at a cell density sufficient to form a cell sheet. Generally, the density of the cells to be seeded is $1.0 \times 10^4$-$5.0 \times 10^6$ cells/cm$^2$, more preferably $2.0 \times 10^4$-$1.0 \times 10^6$ cells/cm$^2$.

A cell sheet composed of CECSi cells obtained by the present invention can form a substitute for the corneal endothelial cell sheet, and can be used as a graft for the treatment of a disease requiring transplantation of corneal endothelium, for example, bullous keratopathy, corneal edema, corneal leukoma and the like.

In another embodiment other than a sheet, the obtained CECSi cells as they are, a cell mass such as pellet obtained by concentration by filtration and the like, and the like are used as the medicament of the present invention. Moreover, it is also possible to add a protector such as glycerol, DMSO (dimethyl sulfoxide), propylene glycol, acetamide and the like to the medicament, and cryopreserve the mixture. For safer utilization of a medicament, the medicament may be subjected to a treatment under the conditions causing denaturation of pathological proteins, such as a heat treatment, a radiation treatment and the like, while retaining the function of the corneal endothelial cell.

EXAMPLE

The present invention is described in detail in the following by referring to Examples, which are not to be construed as limitative. Unless particularly specified, the reagents and materials to be used are commercially available. Abbreviations used in the present specification are the same as those generally used in the pertinent field unless otherwise specified.

Example 1: Difference in Gene Expression Between iPS Cell-Derived Neural Crest Cell and Human Corneal Endothelium by DNA Microarray Using two kinds of cells of (a) genuine human corneal endothelial cells collected from the cornea for overseas donor research and (b) iPS cell-derived neural crest cells (iPS-NCC) induced from iPS cell (FF-I01s01 line; the Center for iPS Cell Research and Application, Kyoto University) by a modified method of the neural crest cell induction method of a previous report (Bajpai et al., Nature. 2010 Feb. 18; 463(7283):958-62), Agilent Technology DNA microarray analysis was outsourced to Hokkaido System Science Co., Ltd., and gene expression profiles were compared by DNA microarray. iPS-NCC (also indicated as iNCC) was confirmed by the expression of neural crest cell markers P75NTR and CD49D. It was newly found that corneal endothelial cells highly express KGF, IGF2, LIF, and IL6 (Tables 2-1, 2-2). It was also found that AP1 (C-FOS+C-JUN), which is considered to be located downstream of STAT3, is highly expressed (Tables 2-1, 2-2).

TABLE 2-1

| | | iNCC (P75NTR, CD49D+/+) | | | overseas donor corneal endothelium | |
|---|---|---|---|---|---|---|
| | | | Normalized | Raw | | Normalized | Raw |
| major transcription factors | Yamanaka 4 factors | SOX2 | 2.710052124 | 5556.1504 | *SOX2* | 0.004124523 | 5.662242 |
| | | *KLF4* | 0.661058842 | 22.516338 | KLF4 | 77.66560915 | 1771.351 |
| | | POU5F1 | 1.225959288 | 163.18112 | POU5F1 | 1.004650984 | 89.54213 |
| | | *MYC* | 0.717896077 | 1484.2257 | MYC | 3.777244311 | 5229.157 |
| | | SOX9 | 1.016324792 | 923.38416 | *SOX9* | 0.034131899 | 20.76485 |
| | | *PITX2* | 0.390170011 | 5.405986 | PITX2 | 1850.847097 | 17171.56 |
| | AP-1 | JUN | 0.798343263 | 1229.7722 | JUN | 8.922683089 | 9203.414 |
| | | FOS | 1.540492438 | 726.9833 | FOS | 72.89285487 | 23033.93 |
| pump function related | mineralocorticoid receptor | *NR3C2* | 0.911577234 | 4.955407 | NR3C2 | 222.7720768 | 810.8954 |
| | Serum/glucocorticoid regulated kinase | *SGK1* | 0.039498383 | 233.3241 | SGK1 | 9.617681163 | 38042.5 |
| | Na,K-ATPase α1 | ATP1A1 | 0.835537161 | 4574.6562 | ATP1A1 | 12.35738435 | 45304.13 |
| surface marker | NGF receptor | NGFR | 16.24279497 | 10037.197 | *NGFR* | 0.074455204 | 30.80813 |
| | CD49C | *ITGA3* | 0.879465482 | 49.69784 | ITGA3 | 64.05654141 | 2423.822 |
| | CD49D | ITGA4 | 1.121630465 | 807.36426 | *ITGA4* | 0.015790777 | 7.610992 |
| | beta adrenoceptors | *ADRB1* | 0.913332142 | 3.8595197 | ADRB1 | 347.9665943 | 984.6018 |
| | | *ADRB2* | 0.534721281 | 28.736946 | ADRB2 | 531.5378068 | 19127.82 |

Those with high expression are shown in bold, and those with low expression are in italics.

TABLE 2-2

| | iNCC (P75NTR, CD49D+/+) | | overseas donor corneal endothelium | |
|---|---|---|---|---|
| | Normalized | Raw | Normalized | Raw |
| | | raw data expression order | | |
| IGF2 | 0.601226 | 14793.12 | 9.719324 | 160131.4 |
| VEGFB | 0.656367 | 9282.305 | 1.584979 | 15008.96 |
| LIF | 0.63778 | 108.0551 | 116.3198 | 13196.11 |
| VEGFA | 0.946234 | 981.665 | 12.22036 | 8489.209 |
| HBEGF | 0.305009 | 26.29994 | 102.2663 | 5904.622 |
| FGF7 | 0.904036 | 40.19233 | 132.6254 | 3948.232 |
| IL6 | 0.860024 | 4.566833 | 983.2306 | 3496.055 |

TABLE 2-2-continued

| | iNCC (P75NTR, CD49D+/+) | | overseas donor corneal endothelium | |
|---|---|---|---|---|
| | Normalized | Raw | Normalized | Raw |
| VEGFA | 0.970134 | 294.6273 | 11.77461 | 2394.452 |
| TGFB1 | 0.086437 | 41.08457 | 5.565507 | 1771.337 |
| FGF10 | 1.117279 | 28.49381 | 45.35161 | 774.4615 |
| PDGFC | 0.571046 | 1721.358 | 0.377421 | 761.8048 |
| PDGFA | 0.844128 | 153.6974 | 4.724392 | 575.9999 |
| FGF9 | 1.11417 | 59.85115 | 10.38938 | 373.7053 |
| FGF2 | 0.997773 | 70.65986 | 6.715243 | 318.4349 |
| PDGFB | 0.269453 | 25.2515 | 3.018807 | 189.4337 |
| TGFB2 | 0.00000 | 91.35399 | 0.604531 | 164.0412 |
| FGF1 | 0.862163 | 54.23782 | 1.139394 | 47.99601 |
| 1GF1 | 0.340819 | 17.71447 | 1.345427 | 46.82558 |
| FGF8 | 0.7112 | 7.493367 | 0.965044 | 6.808487 |
| EGF | 1.040062 | 10.38286 | 0.903624 | 6.040371 |
| VEGFC | 1.151762 | 650.2108 | 0.013788 | 5.212043 |
| HGF | 1.826174 | 129.2054 | 0.108579 | 5.144016 |
| | | normalized data order | | |
| IL6 | 0.860024 | 4.566833 | 983.2306 | 3496.055 |
| FGF7 | 0.904036 | 40.19233 | 132.6254 | 3948.232 |
| LIF | 0.63778 | 108.0551 | 116.3198 | 13196.11 |
| HBEGF | 0.305009 | 26.29994 | 102.2663 | 5904.622 |
| FGF10 | 1.117279 | 28.49381 | 45.35161 | 774.4615 |
| VEGFA | 0.946234 | 981.665 | 12.22036 | 8489.209 |
| VEGFA | 0.970134 | 294.6273 | 11.77461 | 2394.452 |
| FGF9 | 1.11417 | 59.85115 | 10.38938 | 373.7053 |
| IGF2 | 0.601226 | 14793.12 | 9.719324 | 160131.4 |
| FGF2 | 0.997773 | 70.65986 | 6.715243 | 318.4349 |
| TGFB1 | 0.086437 | 41.08457 | 5.565507 | 1771.337 |
| PDGFA | 0.844128 | 153.6974 | 4.724392 | 575.9999 |
| PDGFB | 0.269453 | 25.2515 | 3.018807 | 189.4337 |
| VEGFB | 0.656367 | 9282.305 | 1.564979 | 15008.96 |
| 1GF1 | 0.340819 | 17.71447 | 1.345427 | 46.82558 |
| FGF1 | 0.862163 | 54.23782 | 1.139394 | 47.99601 |
| FGF8 | 0.7112 | 7.493367 | 0.965044 | 6.808487 |
| EGF | 1.040062 | 10.38286 | 0.903624 | 6.040371 |
| TGFB2 | 0.22543 | 91.35399 | 0.604531 | 164.0412 |
| PDGFC | 0.571046 | 1721.358 | 0.377421 | 761.8048 |
| HGF | 1.826174 | 129.2054 | 0.108579 | 5.144016 |
| VEGFC | 1.151762 | 650.2108 | 0.013788 | 5.212043 |
| STAT3 | 0.490586 | 233.7426 | 2.906993 | 927.4393 |
| JUN | 0.798343 | 1229.772 | 8.922683 | 9203.414 |
| JUNB | 0.470655 | 35.72011 | 68.29981 | 3470.946 |
| JUND | 0.313445 | 344.3925 | 3.228466 | 2375.235 |
| FOS | 1.540492 | 726.9833 | 72.89285 | 23033.93 |
| FOSB | 0.87945 | 60.51546 | 406.8141 | 18744.34 |
| FOSL1 | 0.809246 | 38.55826 | 43.27233 | 1380.593 |
| FOSL2 | 0.361295 | 28.54396 | 42.46043 | 2246.233 |

From the results of Table 2-1 and Table 2-2, the present inventors made a hypothesis that the pathway of "LIF and IL6 (=STAT3 pathway activator) expression increase→AP1 (C-FOS+C-JUN) expression increase" actively functions in corneal endothelial cells, attempted induction of CECSi cells by using LIF, IL6, and mineralocorticoid (aldosterone), and examined the expression of each differentiation marker in the obtained cells.

(CECSi Cell Induction Medium)

As the basal medium, DMEM/F2 medium (Nacalai Tesque, #04260-64) was used. As the additives, N-2 MAX Media Supplement (100×) (R&D System Inc., #AR009), ascorbic acid (FUSO Pharmaceutical Industries, Ltd.; ascorbic acid injection (50 μg/mL)), IGF1 (Orphan Pacific; Somazon injection (20 ng/mL)), KGF (Wako Pure Chemical Industries, Ltd., #119-00661 (5 ng/mL)), LIF (Sigma Aldrich, #L5283 (1 ng/mL)), IL6 (Wako Pure Chemical Industries, Ltd.; #099-04631 (1 ng/mL)), adrenaline (Daiichi-Sankyo, bosmin injection (0.5 μg/mL)), dexamethasone (KYOWA Critia, orgadrone injection (38 ng/mL)) and aldosterone (Sigma Aldrich, #A9477 (720 ng/mL)) was added to DMEM/F12 basal medium, and as a scaffold material, a culture dish or culture flask coated with laminin 511-E8 fragment (iMatrix 511, Nippi Corporation) was used at a concentration of 3 μg/ml.

(Induction Protocol)

Y27632 was added to iPS cell medium AK03N (Ajinomoto Co., Inc.) at a concentration of 10 μM (hereinafter to be referred to as AK03N+Y medium). A 6-well plate for culture (Greiner 657160) was coated with iMatrix 511 at a concentration of 6 μg/ml. iPS cells (FF-I01s04 line) was suspended in the AK03N+Y medium at a density of $1.0 \times 10^4$ cells/cm$^2$, and seeded in the 6-well plate. The culture was started in a CO$_2$ incubator at 37° C., and the next day, the medium was replaced with AK03N medium without containing Y27632. Thereafter, the medium was exchanged once every 2 to 3 days, and passaged once a week, using TrypLE-Select (Thermo Fisher Scientific), to a 6-well plate coated with iMatrix 511 at the same density as above. For induction into CECSi, iPS cells from the third passage to the 29th passage were used.

At the start of induction, iPS cells were collected from a 6-well plate using TrypLE-Select and suspended in the above-mentioned CECSi cell induction medium. A 35 mm dish for culture or a 100 mm dish was coated with iMatrix 511 at a concentration of 3 μg/ml, and the suspended iPS cells were seeded at a density of $2.0 \times 10^4$ cells/cm$^2$. Culturing was started in a $CO_2$ incubator at 37° C., and thereafter, the medium was replaced once every 2 to 3 days. Since it takes 14 days or more to reach confluence after the start of induction, experiments were performed without passage in Examples 1 to 3.

(Quantitative PCR)

CECSi cells on a 35 mm dish 12 days after the start of induction were subjected to RNA extraction using RNeasy mini kit (#74106), QIAGEN, and cDNA synthesis was performed using ReverTra-plus- (#PCR501), TOYOBO. As the Primer, Random Primer was used, reaction scale 20 μL, 42° C. 20 min×1, 99° C. 5 min×1.

The produced cDNA was subjected to quantitative PCR using ABI Step One Plus using THUNDERBIRD SYBR qPCR Mix (#QPS201), TOYOBO. reaction scale 20 μL, 95° C. 10 min, (95° C. 3 sec, 60° C. 30 sec)×40.

The sequences of the main primers used for quantitative PCR are shown in the following Table.

TABLE 3

| | | | | |
|---|---|---|---|---|
| POU5F1 | NM_002701 | OCT 4 | Fw | GAAACCCACACTGCAGCAGA (SEQ ID NO: 1) |
| | | | Rv | TCGCTTGCCCTTCTGGCG (SEQ ID NO: 2) |
| KLF4 | NM_004235 | KLF4 | Fw | TGCGGCAAAACCTACACAAAG (SEQ ID NO: 3) |
| | | | Rv | GGGCGAATTTCCATCCACAG (SEQ ID NO: 4) |
| MYC | NM_002467 | C-MYC | Fw | GGACCCGCTTCTCTGAAAGG (SEQ ID NO: 5) |
| | | | Rv | TAACGTTGAGGGGCATCGTC (SEQ ID NO: 6) |
| SOX2 | NM_003106 | SOX2 | Fw | GCGCCCTGCAGTACAACTC (SEQ ID NO: 7) |
| | | | Rv | CGGACTTGACCACCGAACC (SEQ ID NO: 8) |
| SOX9 | NM_000346 | SOX9 | Fw | AACGCCTTCATGGTGTGG (SEQ ID NO: 9) |
| | | | Rv | TCTCGCTCTCGTTCAGAAGTC (SEQ ID NO: 10) |
| LIN28A | NM_024674.4 | LIN28A | Fw | TCCGAACCAACCCTTTGCC (SEQ ID NO: 11) |
| | | | Rv | CAAACTGCTGGTTGGACACG (SEQ ID NO: 12) |
| PITX2 | NM_153426 | PITX2 | Fw | CTCCTGAGAGCCGAAAAGAGG (SEQ ID NO: 13) |
| | | | Rv | ATTCTTCCCCTGCTGGCTTTT (SEQ ID NO: 14) |
| JUN | NM_002228 | C-JUN | Fw | GAGCTGGAGCGCCTGATAAT (SEQ ID NO: 15) |
| | | | Rv | CCCTCCTGCTCATCTGTCAC (SEQ ID NO: 16) |
| FOS | NM_005252 | C-FOS | Fw | TACTACCACTCACCCGCAGA (SEQ ID NO: 17) |
| | | | Rv | CGTGGGAATGAAGTTGGCAC (SEQ ID NO: 18) |
| NR3C2 | NM_000901.4 | NR3C2 | Fw | TGAGCTGGAGATCGTACAAACA (SEQ ID NO: 19) |
| | | | Rv | GTGCATCCCCTGGCATAGTT (SEQ ID NO: 20) |
| SGK1 | NM_005627.3 | SGK1 | Fw | GCCTGCCGCCTTTTTATAGC (SEQ ID NO: 21) |
| | | | Rv | CAGGAGGTGTCTTGCGGAAT (SEQ ID NO: 22) |
| ATP1A1 | NM_000701.7 | ATP1A1 | Fw | CCAAAGACAGGGTGCTATCG (SEQ ID NO: 23) |
| | | | Rv | TTGCTTGGACACATCTGAGC (SEQ ID NO: 24) |
| ITGA3 | NM_005501.2 | ITGA3 | Fw | GGTGCCTACAACTGGAAAGG (SEQ ID NO: 25) |
| | | | Rv | GCCTACCTGCATCGTGTACC (SEQ ID NO: 26) |
| ADRB2 | NM_000024 | ADRB2 | Fw | TTTTGGCAACTTCTGGTGCG (SEQ ID NO: 27) |
| | | | Rv | GATCACGCACAGGGTCTCAA (SEQ ID NO: 28) |

Figure 2:
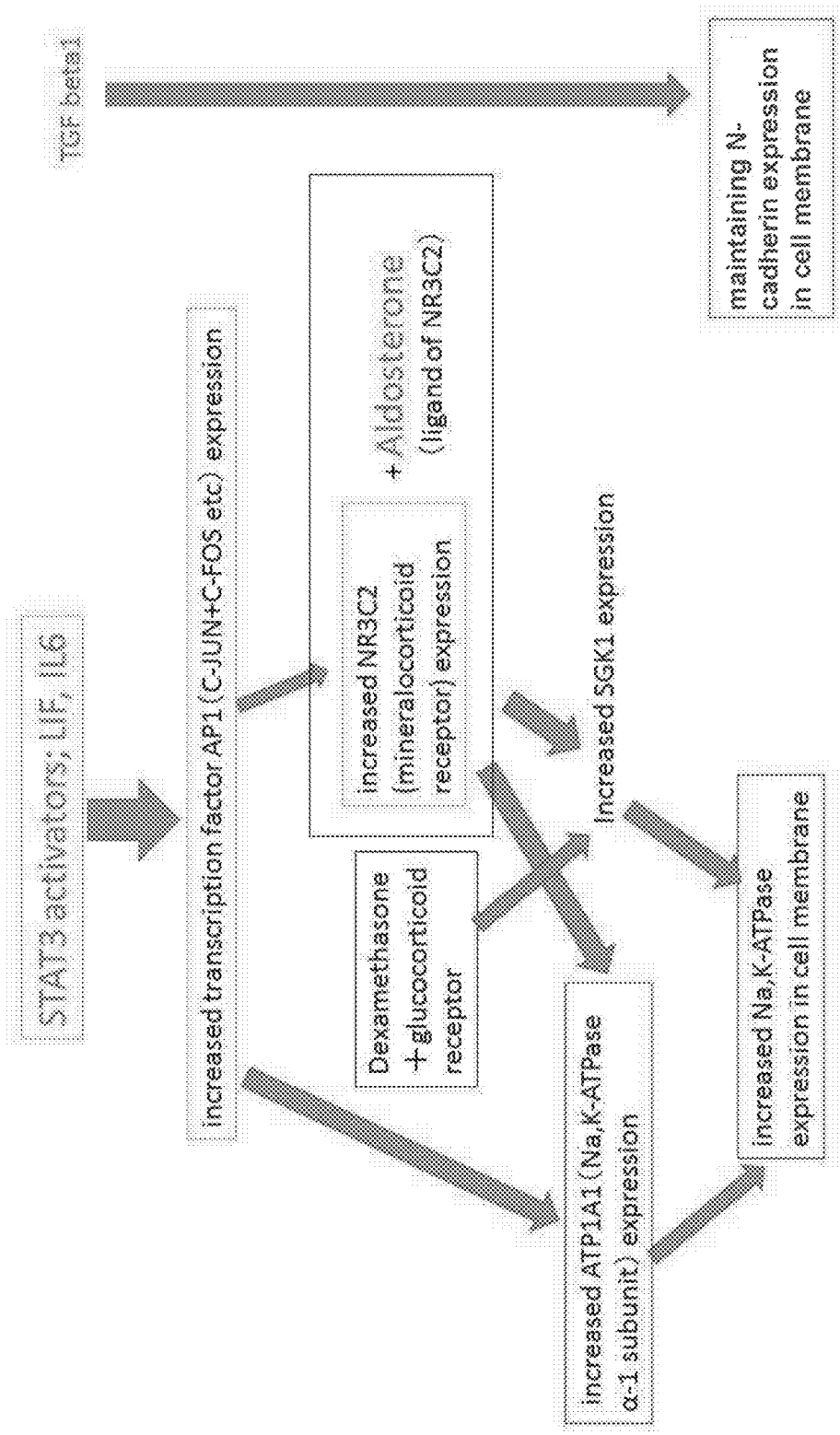
FIG. 2 schematically shows a signal transduction pathway that plays a key role in inducing differentiation into CECSi cells.

As a result, in CECSi cells, increased expression of C-FOS, C-JUN, increased expression of mineralocorticoid receptor (NR3C2), and increased expression of SGK1 at the downstream of NR3C2 were observed, and it was found that the expression of the target Na,K-ATPase α1 subunit (ATP1A1) increased to a level equivalent to that of corneal endothelial cells (FIG. 1). That is, it was found that the activation of the pathway "LIF, STAT3 expression increase-+AP1 expression increase-+NR3C2 expression increase" and the addition of mineralocorticoid, which is a ligand for NR3C2, can sufficiently increase the expression of Na,K-ATPase α1 subunit (ATP1A1) in CECSi cells (FIG. 2).

Figure 3:
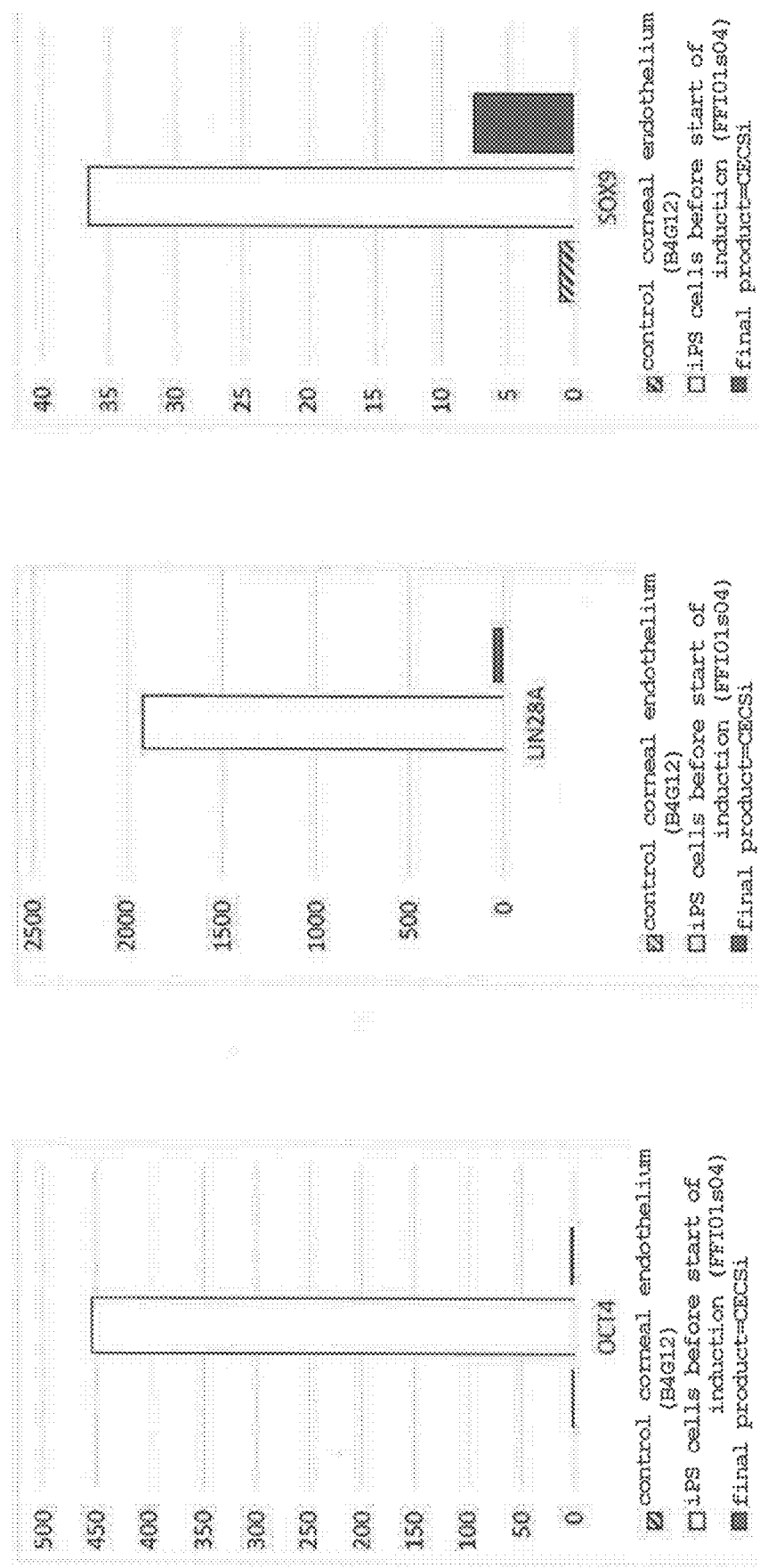
FIG. 3 shows changes in the gene expression in induction of differentiation into CECSi cells. Respective bars show, from the left, the results of B4G12 cells (corneal endothelial cell line) to be the control, FF-I01s04 line (iPS cell) (FFI01s04) before induction, and FF-I01s04 line (iPS cell) (CECSi) on day 12 from the differentiation induction. A decrease in the expression of undifferentiated marker gene was confirmed along with the differentiation induction.

Furthermore, changes in OCT4 and LIN28A, which are undifferentiated markers, and Sox9, which is a non-target cell marker, are shown in FIG. 3. Both were expressed in iPS cells before induction, and confirmed to show significantly decreased expression after induction.

Example 2: Expression of ATP1A1, ZO-1, N-Cadherin and PITX2 11 Days after CECSi Cell Induction According to the induction protocol used in Example 1, iPS cells (FF-I01s04 line) were induced to differentiate. The expression of ATP1A1, ZO-1, N-cadherin and PITX2 was examined using cells on day 11 from the differentiation induction.

(Immunostaining)

CECSi cells on a 35 mm dish were fixed with ice-cooled 4% paraformaldehyde after removing the medium. After washing the dish twice with PBS, a blocking solution (PBST containing 10% Normal Donkey Serum (10% NDS/PBST)) was added and blocking was performed for 30 min. Then, the primary antibody reaction was performed at room temperature for 1 hr with the following antibody amounts.
 (i) ZO1, Na,K,ATPase α1 double staining
  Rabbit anti human ZO-1; Invitrogen, 40-2200, 1:500, 1.5 μL/dish
  Mouse anti human Na,K-ATPase α1; Novus, NB300-146, 1:500, 1.5 μL/dish
  blocking solution (10% NDS/PBST), 0.75 mL/dish
 (ii) N-cadherin, PITX2 double staining
  Rabbit anti human PITX2; Aviva, ARP32431, 1:500, 1.5 μL/dish
  Mouse anti n-cad; Pierce Thermo, MA1-2002, 1:500, 1.5 μL/dish
  blocking solution (10% NDS/PBST), 0.75 mL/dish Next, after washing the dish twice with PBS, the secondary antibody reaction was performed at room temperature for 1 hr with the following antibody amounts.

Donkey anti-rabbit Cy-3, Jackson, 711-165-152, 1:200, 3.75 μL/dish

Donkey anti-mouse Alexaflour488, Invitrogen, A21202, 1:200, 3.75 μL/dish

DAPI, 1:1000, 0.75 μL/dish blocking solution (10% NDS/PBST), 0.75 mL/dish

Then, after washing twice with PBS, the cover glass was mounted with a mounting agent and observed with a fluorescence microscope.

Figure 4:
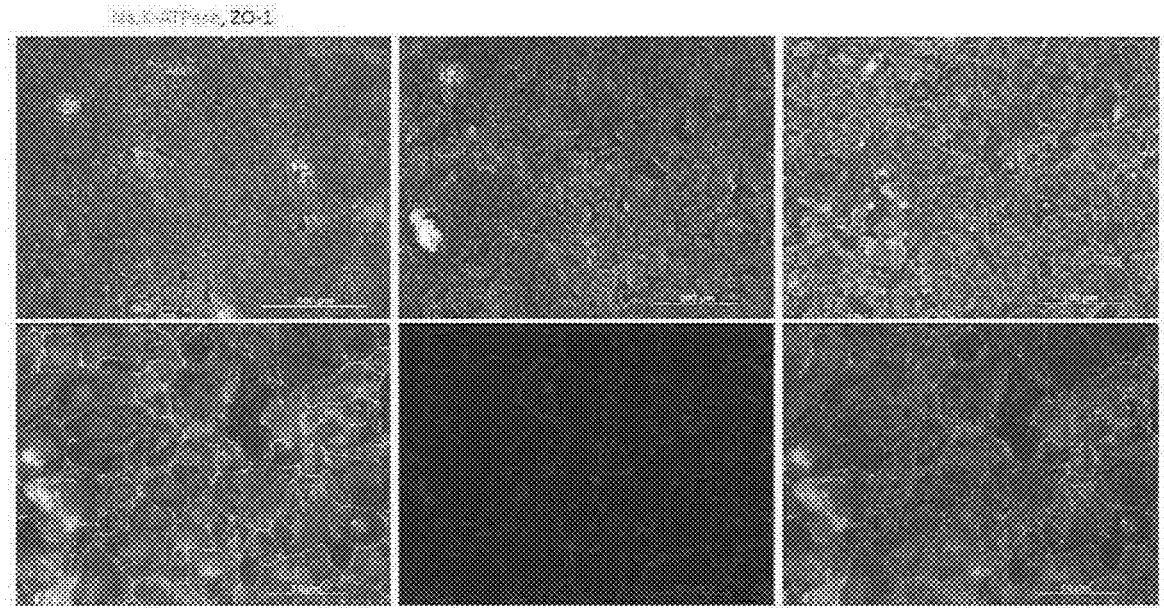
FIG. 4 is a micrograph showing the examination results of the expression of Na,K-ATPase and ZO-1 in FF-I01s04 line (iPS cell) on day 11 from the induction of differentiation into CECSi cells. It was found that 90% or more of the cells showed good expression of Na,K-ATPase and ZO-1.
Figure 5:
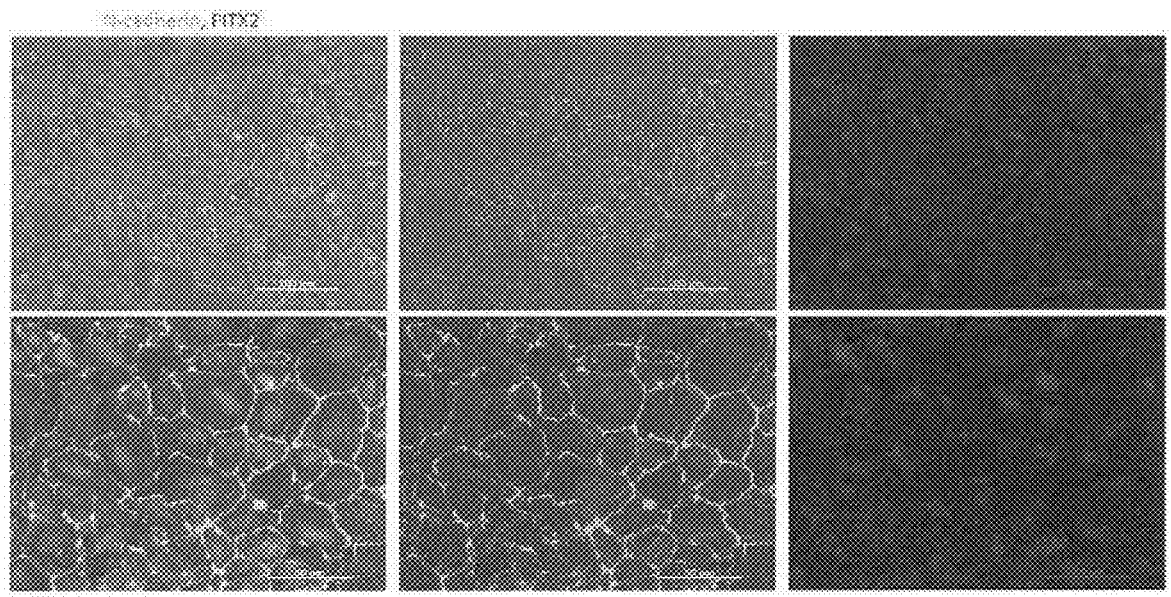
FIG. 5 is a micrograph showing the examination results of the expression of N-cadherin and PITX2 in FF-I01s04 line (iPS cell) on day 11 from the induction of differentiation into CECSi cells. It is clear that N-cadherin formed an adherence junction.

The results are shown in FIG. 4 (ATP1A1, ZO-1) and FIG. 5 (N-cadherin, PITX2). CECSi cells that show an Na,K-ATPase gene expression level equivalent to that of corneal endothelial cells, express Na,K-ATPase on the cell membrane, form a tight junction, and that form an adherens junction by N-cadherin could be induced with almost 100% efficiency from iPS cells already on day 11 from the start of induction, by merely continuing to culture the iPS cells in a CECSi cell induction medium containing the above-mentioned components, and one type of scaffold material (iMatrix 511). When nuclear expression of transcription factor PITX2, which is one of the corneal endothelial cell markers, was manually counted by immunostaining, it was also expressed in 100% of the cells.

Example 3: Evaluation of Induction Efficiency into CECSi Cells (Verification by FACS)

Furthermore, induction efficiency was quantitatively evaluated by performing flow cytometry using integrin alpha-3 (CD49c) expressed on corneal endothelial cells as a surface antigen.

(Flow Cytometry)

After collecting CECSi cells on 10 cm dish with Accutase, the cells were washed by adding HESS and centrifuging and discarding the supernatant. After suspending the cells in HBSS, 2 μL of each of the following antibody reagents was added to $1 \times 10^6$ cells/100 μL of cell suspension.

PE anti-human CD49c, BioLegend #343803

PE anti-human CD49d, Biolegend #304304

Alternatively, 2 μL of rBC2LCN-FITC (Wako Pure Chemical Industries, Ltd. #80-02991) was added. The antibody reaction was performed at room temperature for 1 hr.

The cells were washed by adding HBSS and centrifuging and discarding the supernatant, and flow cytometry was performed using SH800 manufactured by SONY.

Figure 6:
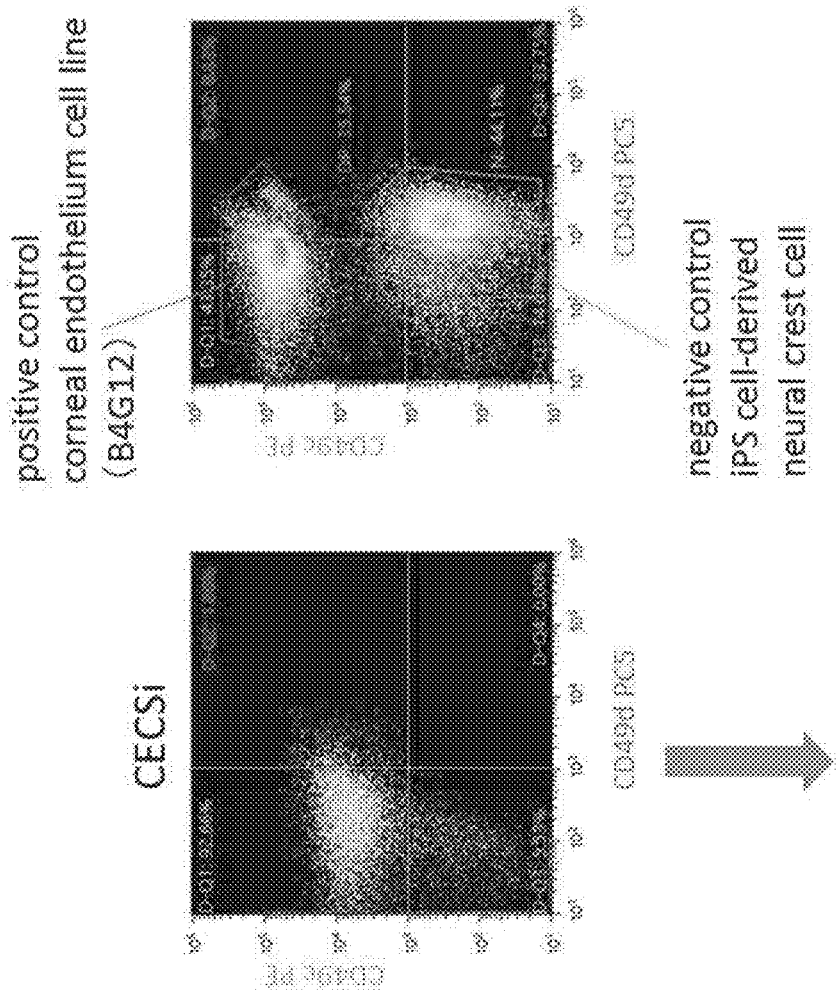
FIG. 6 shows quantitative evaluation of the efficiency of inducing differentiation into CECSi cells by flow cytometry using integrin alpha-3 (CD49c) expressed in corneal endothelial cells as a surface antigen.

The results are shown in FIG. 6. The cells induced by the CECSi cell induction medium containing the above-mentioned components showed an induction efficiency of 93% by CD49c. On the other hand, since neural crest cells derived from iPS cells are positive for integrin alpha-4 (CD49d), CECSi induced by the method of the present invention is closer to real corneal endothelial cells as compared with neural crest cells.

Figure 7:
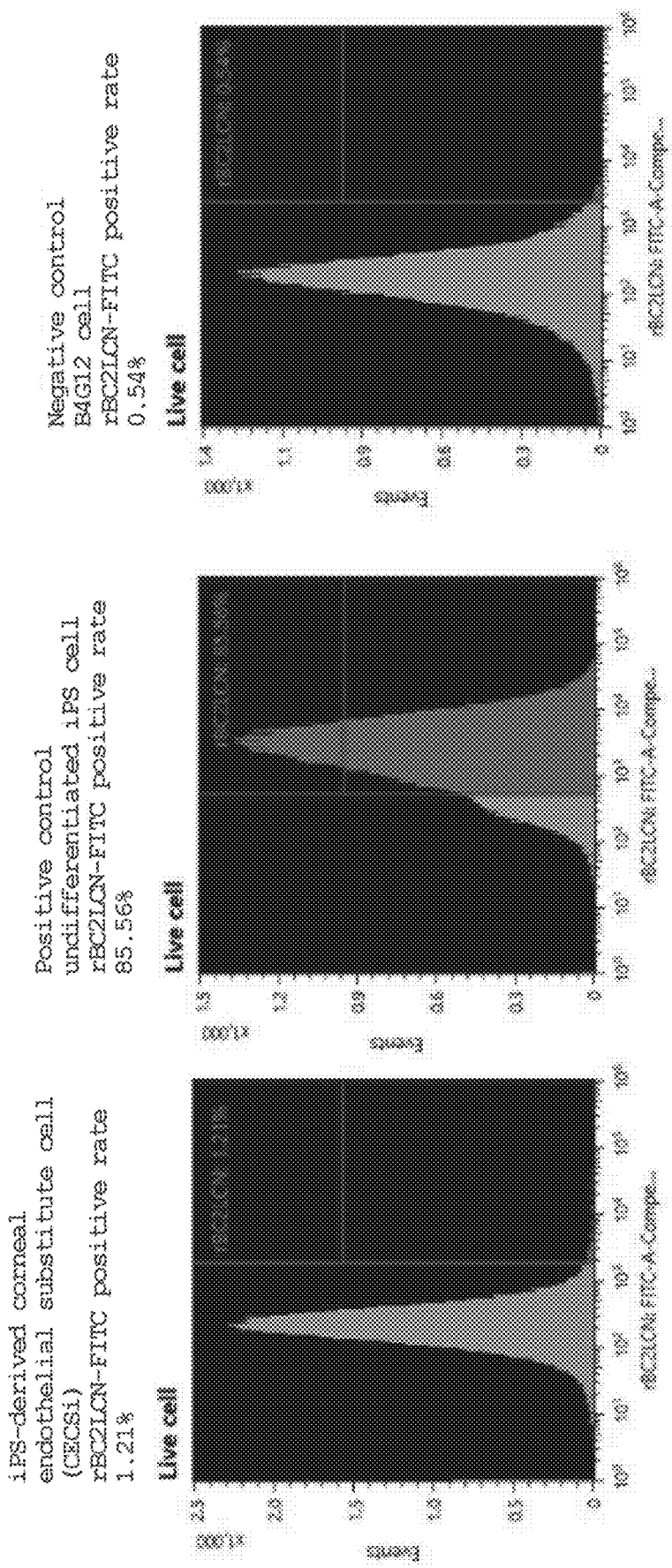
FIG. 7 shows the evaluation results of the positive rate of undifferentiated cells after differentiation induction by flow cytometry using rBC2LCN-FITC.

Furthermore, the undifferentiated cell positive rate was evaluated by flow cytometry using rBC2LCN-FITC. rBC2LCN has a high affinity for H-type3 (Fucα1-2Galβ1-3GalNAc), which is a mucin-like O-type sugar chain on podocalyxin present on the surface of human ES/iPS cells, and is therefore used as a marker of undifferentiated human ES/iPS cells. The results are shown in FIG. 7. It is clear that iPS cells were efficiently induced into CECSi cells by the method of the present invention.

Example 4: Effect of TGF-Beta 1

Using a medium (hereinafter referred to as CECSi cell induction (+T) medium) obtained by adding TGF-beta 1 (R&D System Inc., #240-GMP (1 ng/mL)) to the differentiation induction medium prepared in Example 1, the effect thereof was investigated.

Induction of iPS cells (FF-I01s04) was started using CECSi cell induction medium or CECSi cell induction (+T) medium, and the first passage was performed on day 11 and the second passage was performed on day 15 from the start of induction. At the time of passage, the cells were collected using Accutase (Nacalai Tesque #12679-54), and suspended and seeded at a density of $1.5 \times 10^5$ cells/cm$^2$ in a 35 mm dish or 100 mm dish coated with iMatrix 511 at a concentration of 3 μg/ml, without changing the previous medium.

Figure 8:
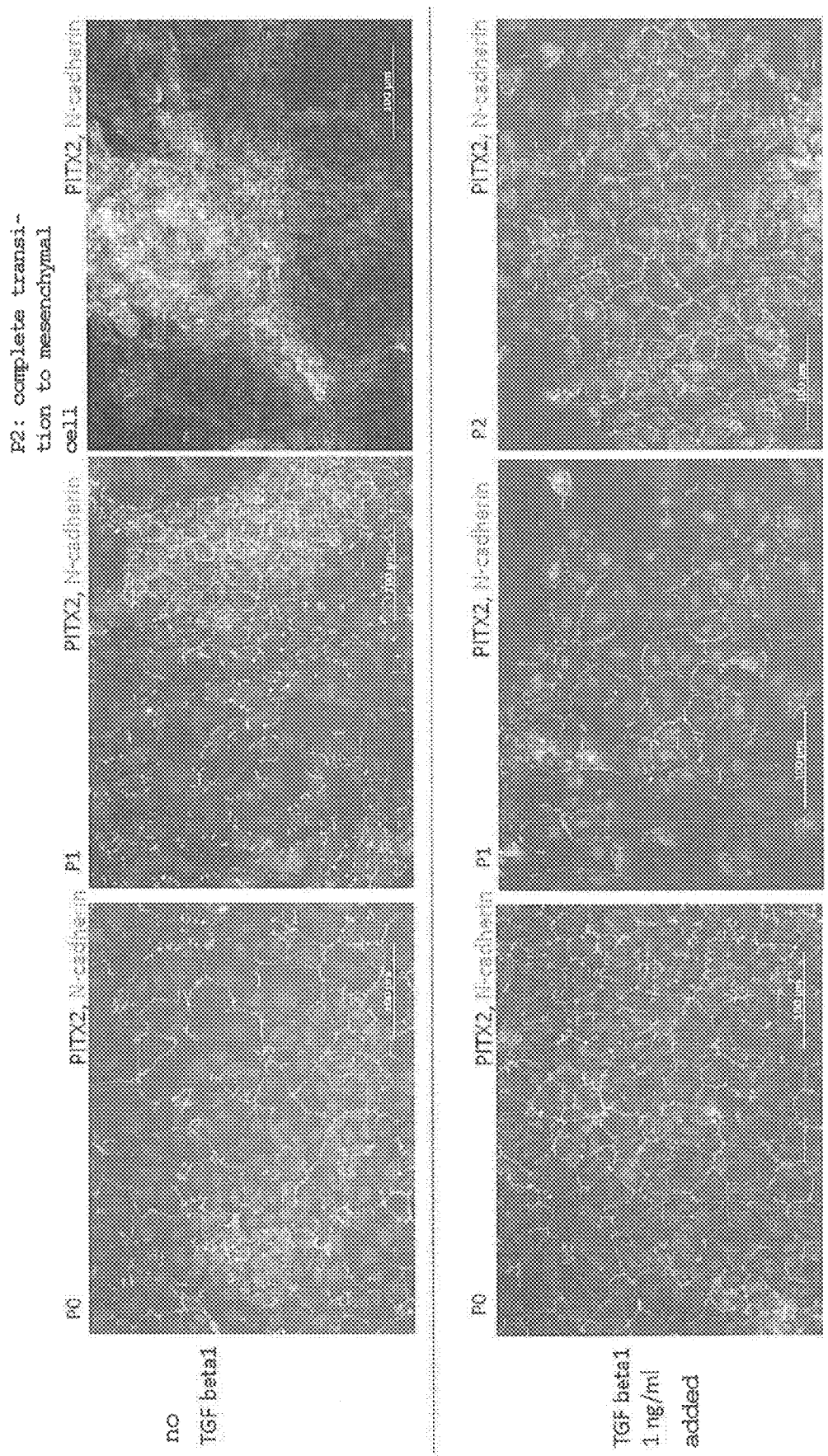
FIG. 8 is a micrograph showing the examination results of the expression of N-cadherin and PITX2 in the presence of TGF-beta 1 on day 11 from the differentiation induction into CECSi cells. The cells could be favorably induced to differentiate into CECSi cells even when passaged iPS cells were used.

At day 15 (after the first passage) and day 17 (after the second passage) from the start of induction, the expression state of N-cadherin and PITX2 was examined by immunostaining in the same manner as in Example 2. The results are shown in FIG. 8.

It was found that, by adding TGF-beta 1, the expression of N-cadherin was maintained and the endothelial morphology could be maintained even after passage.

Experimental Example 1: Differentiation Induction Inhibitory Activity of bFGF

Figure 9:
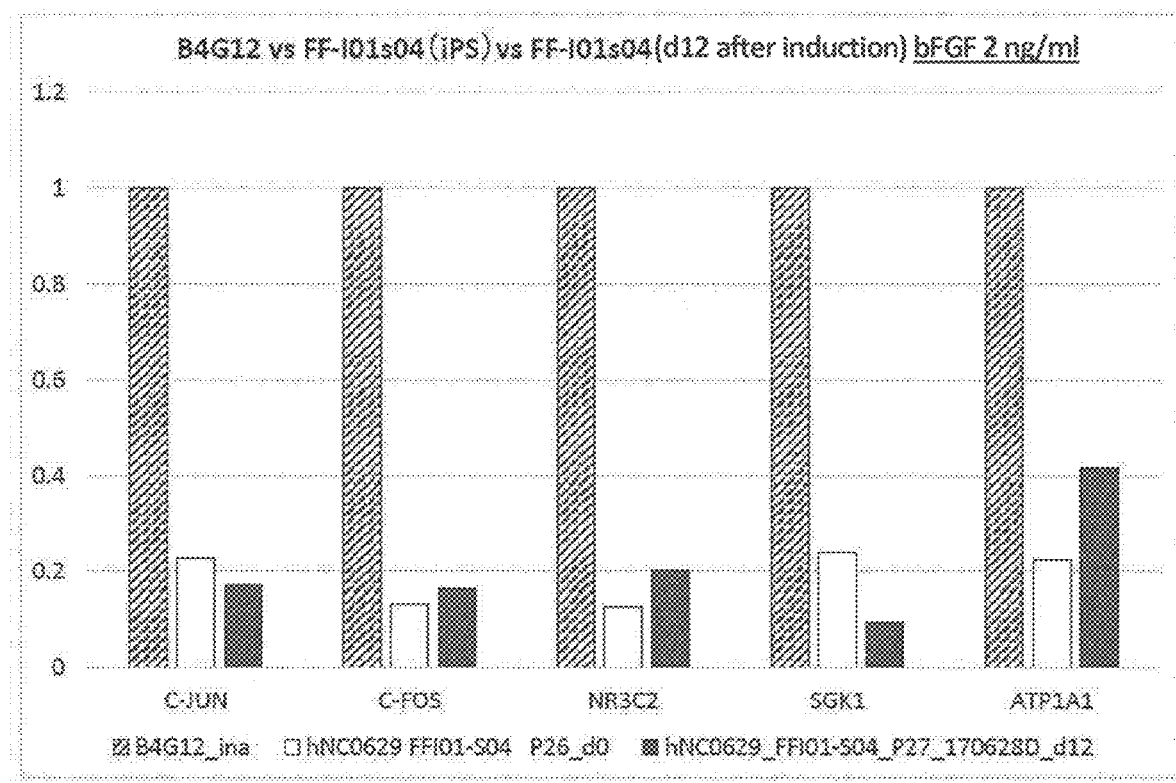
FIG. 9 shows changes in the gene expression in induction of differentiation into CECSi cells in the presence of bFGF2. Respective bars show, from the left, the results of B4G12 cells (corneal endothelial cell line) (B4G12_ina), FF-I01s04 line (iPS cell) (hNC0629 FFI01-S04 P26_d0) before induction, and FF-I01s04 line (iPS cell) (hNC0629_FFI01-S04_P27_170628D_d12) on day 12 from the differentiation induction.

In the same manner as in Example 1 except that a medium containing bFGF (2 ng/mL) was used, the expression of each gene was quantified. The results are shown in FIG. 9. As is clear from the results, when bFGF was added, an increase in ATPA1 or NR3C2 expression was not observed, and therefore an increase in ATP1A1 expression, which is important as the function of corneal endothelial cells, was not observed, either.

The expression of ATP1A1 and ZO-1 in the cells cultured in a medium containing bFGF was examined in the same manner as in Example 2. Elongated cells poorly expressing ZO-1 appeared, and the expression of ATP1A1 was remarkably low.

From these results, it was found that it is important not to add bFGF in inducing differentiation into CECSi cells.

Experimental Example 2: Differentiation Induction Inhibitory Activity of ROCK Inhibitor In the same manner as in Example 2 except that a medium containing fasudil (50 μM), which is a ROCK inhibitor, was used, the expression of ATP1A1 and ZO-1 was examined. Elongated cells poorly expressing ZO-1 appeared, and the expression of ATP1A1 in the cellular membrane was low.

From these results, it was found that it is effective not to add a ROCK inhibitor in inducing differentiation into CECSi cells.

Figure 10:
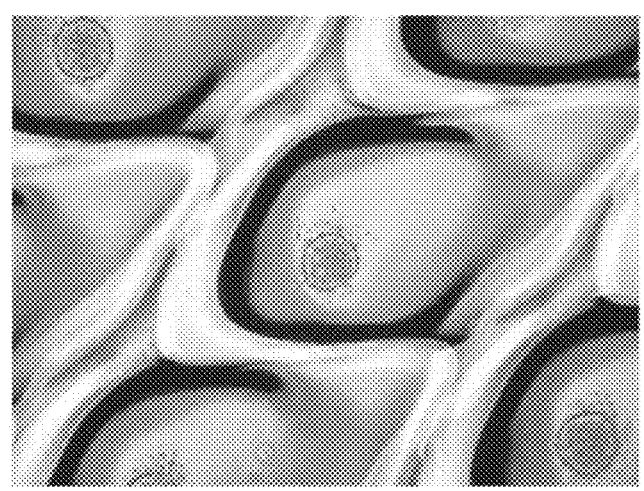
FIG. 10 is a micrograph showing the appearance of spheroids produced after thawing a cryopreserved cell stock. The spheroid formation became possible by answering the cryopreserved cell stock and immediately shifting to suspension culture.

Example 5: Maintenance of Cell Morphology after Cryopreservation and Thawing of CECSi Cells By a method similar to that in Example 4, CECSi cells were induced using a CECSi cell induction (+T) medium, and passaged once on day 10 after induction, and the cells were collected on day 14 using Accutase (Nacalai Tesque #12679-54). The cells were suspended in a cell preservation solution, Banbanker hRM (Nippon Genetics #CS-07-001), at a density of $1\times10^7$ cells/ml and cryopreserved in a deep freezer at −80° C. After 3 days, the cryopreserved cells were thawed and immediately thereafter suspended in a medium obtained by adding a ROCK inhibitor Y27632 (Wako Pure Chemical Industries, Ltd., 039-24591) to the CECSi cell induction (+T) medium at a concentration of 10 μM (hereinafter to be referred to as CECSi cell induction (+TY) medium), and seeded in EZsphere 10 cm dish (AGC TECHNO GLASS Co., Ltd., 631-35201) at a cell number of $3\times10^5$ cells/dish (=200 cells per EZsphere 1 well cell number per one spheroid). This was performed 3 times (once on Oct. 30, 2017, twice on Nov. 7, 2017), and the percentage of viable cells after thawing was 91%, 86%, 94%, and the average viable cell percentage of 3 times was 90.3%. By culturing the cells in an incubator at 37° C. for one day, spheroids (cell aggregates) of CECSi cells were formed (FIG. 10). The CECSi cell spheroids were suspended and seeded in a 35 mm dish coated with iMatrix 511 at a concentration of 3 μg/ml in a CECSi cell induction (+T) medium at a density of $1.5\times10^5$ cells/cm$^2$.

Two days after seeding, ZO1, Na,K,ATPase α1 double staining, N-cadherin and PITX2 double staining were performed in the same manner as in Example 2, and the expression state of these was examined by immunostaining. The results are shown in FIG. 11. It was confirmed that the cells develop while maintaining the formation of tight junction by ZO-1 and adherens junction by N-cadherin, maintaining the expression of Na,K,ATPase α1 on the cell membrane, and maintaining the expression of PITX2 in the cell nucleus. It was confirmed that the cell morphology can be maintained by this method even after freezing and thawing of the cells.

Example 6: Efficacy Evaluation Using Rabbits of CECSi Cell Spheroids after Cryopreservation and Thawing By a method similar to that in Example 4, Example 5, the cells were passaged once on day 11 from the start of induction, and the CECSi cells were cryopreserved on day 19.

One month later, this cell stock was thawed and spheroidized by a method similar to that in Example 5, and the spheroid was collected by centrifugation at 400G for 10 min. The spheroid in an amount equivalent to $3\times10^5$ cells in terms of cell number was mixed with 160 μl of a base substrate composed of the following components (hereinafter "transplantation substrate") to produce a Spheroid suspension.

intraocular perfusion (Opeguard, Senju Pharmaceutical Co., Ltd.) 80 μl
  viscoelastic substance for ophthalmic surgery (Shellgan, Santen Pharmaceutical Co., Ltd.) 80 μl
  insulin (novolin R100, NOVO NORDISK) final concentration 0.1 U/ml
  IGF1 (Orphan Pacific, somazon) final concentration 20 ng/mL adrenaline (Daiichi-Sankyo, bosmin) 0.5 μg/ml
  sodium ascorbate (FUSO Pharmaceutical Industries, Ltd., vitamin C injection "FUSO") 25 μg/ml After producing the Spheroid suspension, it was filled in a Terumo FN syringe and stored in a refrigerator at 4° C. for one day.

As a negative control for transplantation experiment, rabbit corneal endothelial cells were cultured in a medium of the following components (hereinafter EMT medium), the cells that underwent epithelial-mesenchymal transition were collected, $3\times10^5$ cells were mixed with 160 μl of the transplantation substrate, and the mixture was filled in an FN syringe and stored in a refrigerator at 4° C. for 1 day (hereinafter EMT-RCE).

1. DMEM/F12 (Nacalai Tesque, #08460-95)
 2. 10% FBS (Sigma-Aldrich #F7524)
 3. Pen/strep/amphotericin B (Sigma-Aldrich #A5955)1×
 4. L-Ala-L-Glu 2 mM (Nacalai Tesque, #04260-64)
 5. ITS supplement 1× (Sigma-Aldrich #I3146)
 6. bFGF 20 ng/mL (Miltenyi #MG-130-093-841)
 7. TGFb1 1 ng/mL (R&D System Inc., #240-GMP)

The next day, a transplantation experiment to rabbit was performed. The corneal endothelial cells of the left eye of the rabbit were scraped off by rubbing a range of 8 mm in diameter with a soft tapered needle for ophthalmic surgery. After washing the anterior chamber with physiological saline, CECSi cell spheroid ($3\times10^5$ cells per eye/transplantation substrate 160 μl) or rabbit EMT endothelial cell (also $3\times10^5$ cells per eye/transplantation substrate 160 μl) was injected into the anterior chamber. 4 rabbits and 4 eyes each of the both groups received the injection. For 3 hours immediately after the operation, the transplanted eye was positioned downward and the cells were deposited on the posterior surface of the cornea to allow for engraftment. The thickness of the central cornea was measured with an ultrasonic pachymeter and the anterior eye was photographed 1, 2, 6, 8, and 13 days after surgery.

Figure 13:
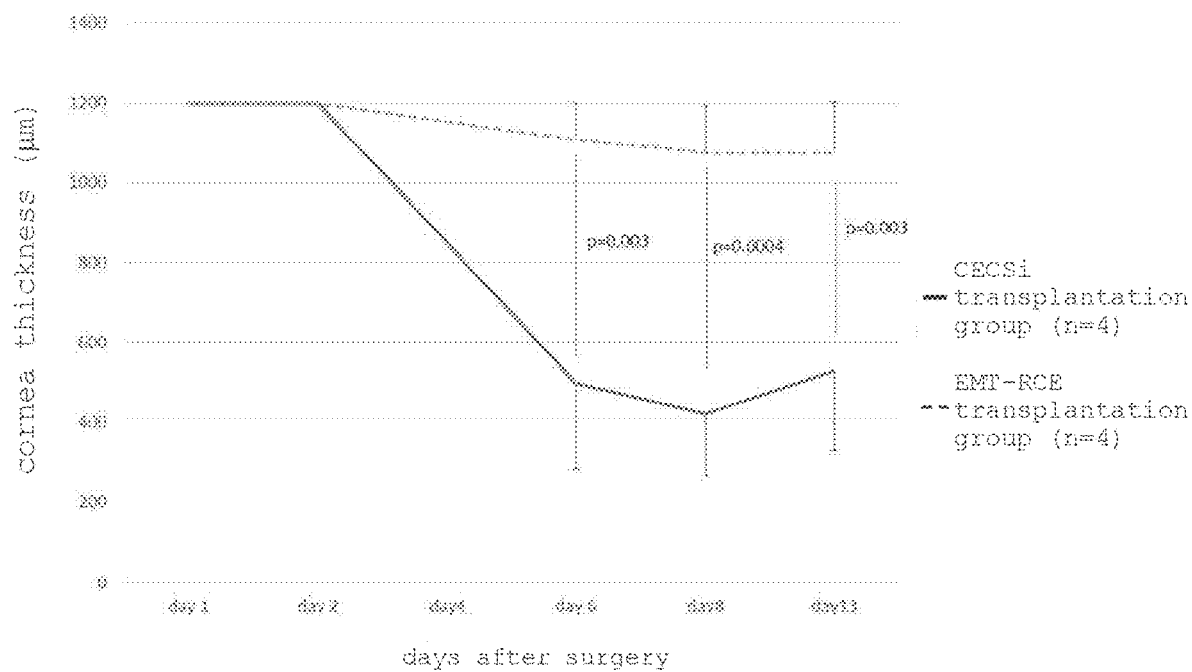
FIG. 13 shows the results of changes in the corneal thickness in an experiment of CECSi cell spheroid transplantation onto the posterior surface of a rabbit cornea. The corneal thickness, which was thickened by corneal edema, decreased by day 6 to day 13 after transplantation.
Figure 14:
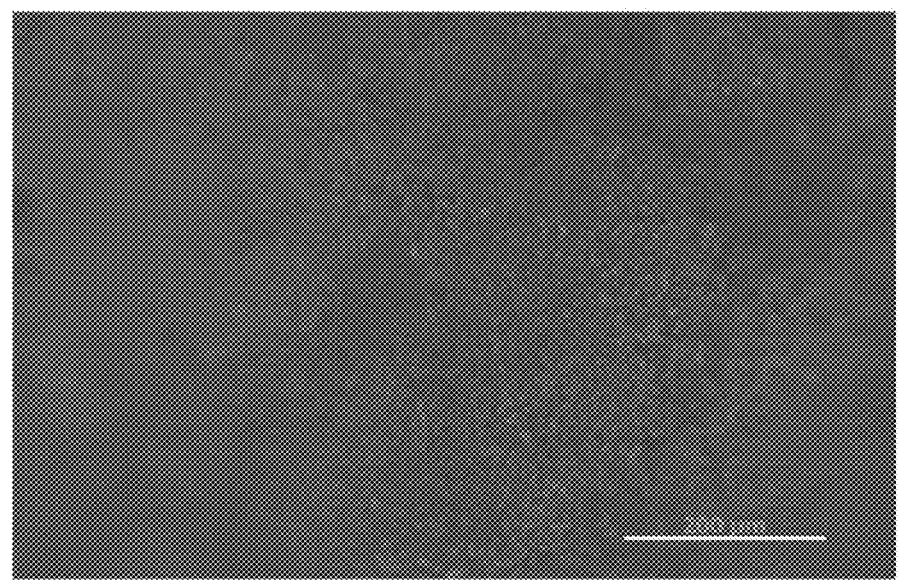
FIG. 14 is a micrograph showing the results of immunostaining a rabbit cornea with a mouse anti-human nuclear antibody on day 14 after transplanting CECSi cell spheroids to the posterior surface of the cornea, and cutting out the cornea on day 14. The central part of the posterior surface of the cornea was covered with human-derived cells with red-stained nuclei, and it was confirmed that the transplanted CECSi cells were engrafted.

The photographs of the anterior eye are shown in FIG. 12. In the EMT-RCE transplantation group as the negative control, edematous clouding of the cornea persisted during the observation period. On the other hand, in the CECSi cell spheroid transplantation group, the edematous clouding that persisted until 2 days after the surgery was recovered, and the transparency of the cornea was recovered after 6 days. The results of changes in corneal thickness are shown in FIG. 13. In the EMT-RCE transplantation group as the negative control, the corneal thickness was maintained at not less than 1000 μm due to corneal edema during the observation period. On the other hand, in the CECSi cell spheroid transplantation group, the corneal thickness was high until 2 days after the surgery, but thereafter decreased as the corneal edema was improved and the transparency was recovered. From 6 to 13 days after the surgery, the corneal thickness was significantly lower than that in the negative control.

The CECSi cell-transplanted eye was collected on day 14 after the surgery, and the engraftment of the transplanted cells was confirmed by immunostaining with an anti-human nuclear antibody by the following procedure.

(Confirmation of Engraftment of Transplanted CECSi Cells by Immunostaining)

The cornea was cut out from said transplanted eye, placed in a well of a 12-well plate, washed once with PBS, and then fixed with ice-cold 4% paraformaldehyde. After washing the well twice with PBS, a blocking solution (PBST containing 10% Normal Donkey Serum (10% NDS/PBST)) was added and blocking was performed for 30 min. Then, the primary antibody reaction was performed at room temperature for 1 hr with the following antibody amounts.

(i) Human Nuclear Staining
  Mouse anti human Nuclei; Abnova, MAB8178, 1 μL/well blocking solution (10% NDS/PBST), 0.5 mL/well Then, after washing the dish twice with PBS, a secondary antibody reaction was performed at room temperature for 1 hr with the following antibody amounts.

Donkey anti-mouse Cy-3, Jackson, 715-165-151, 1:200, 2.5 μL/well
  DAPI, 1:1000, 1 μL/well blocking solution (10% NDS/PBST), 0.5 mL/well Thereafter, after washing twice with PBS, the cornea was placed on the slide, the cover glass was mounted with a mounting agent, and the cornea was observed with a fluorescence microscope.

The results are shown in FIG. 13. The central portion of the cornea was covered with human-derived cells with the cell nucleus stained with an anti-human nuclear antibody (red). Thus, it was confirmed that the transplanted CECSi cells were engrafted during this observation period.

Example 7: Expression of ATP1A1, ZO-1, N-Cadherin and PITX2 11 Days after CECSi Cell Induction According to the induction protocol used in Example 1, iPS cells (FF-I01s04 line or MH09s01 line) were induced to differentiate. The expression of ATP1A1, ZO-1, N-cadherin and PITX2 was examined in the same manner as in Example 2 by performing immunostaining using each antibody and the cells on day 11 from the differentiation induction. The MH09s01 line was obtained from the Center for iPS Cell Research and Application, Kyoto University.

Figure 15:
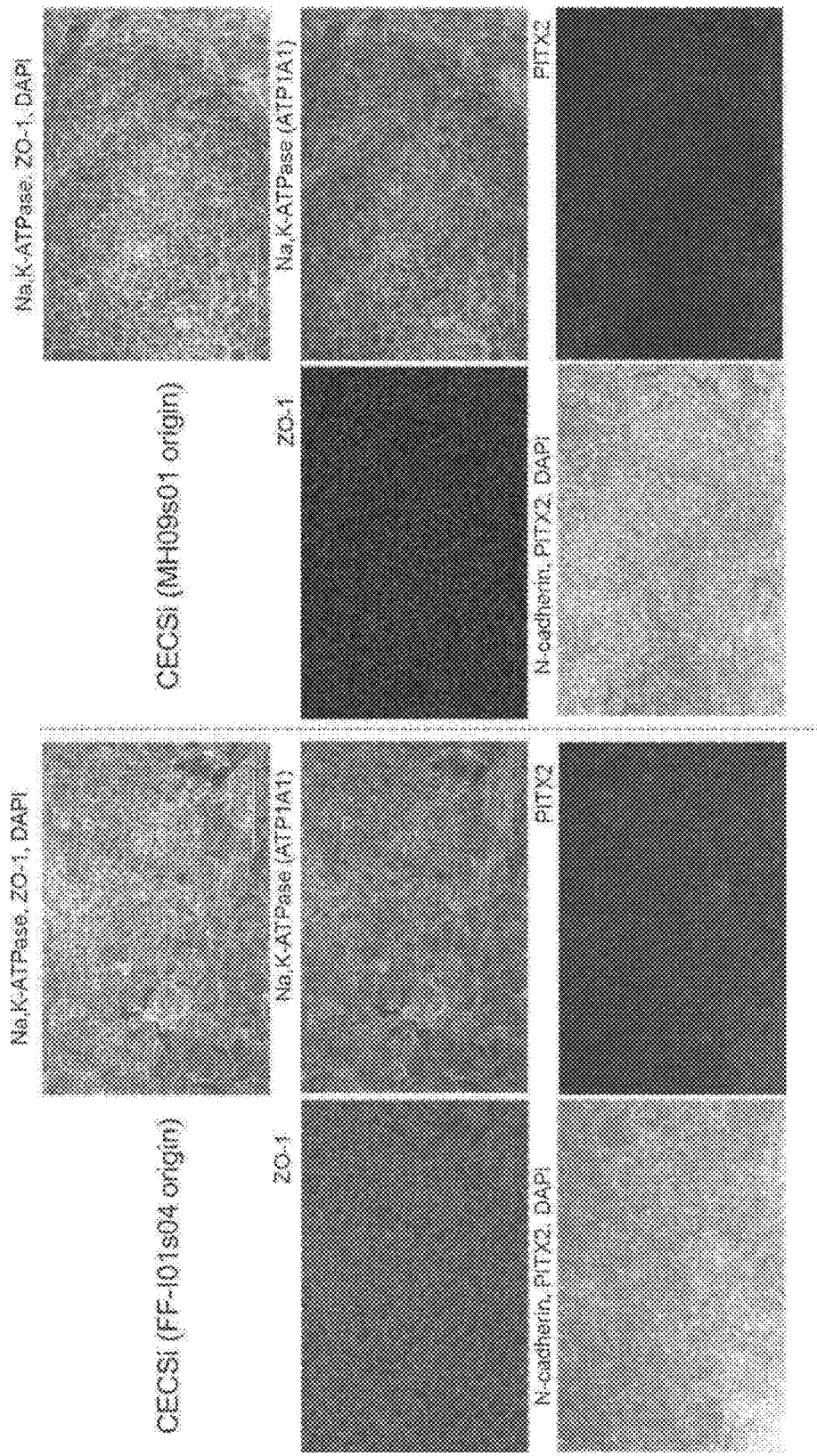
FIG. 15 is a micrograph showing the examination results of the expression of Na,K-ATPase, ZO-1, N-cadherin and PITX2 in FF-I01s04 line (iPS cell) and MH09s01 line (iPS cell) on day 11 from the induction of differentiation into CECSi cells. It could be confirmed that cells (CECSi cells) having similar characteristics are obtained regardless of which iPS cell line is used as a starting material for inducing differentiation.

The results are shown in FIG. 15. It was found that similar CECSi cells can be produced by the method of the present invention even when different kind of iPS cells are used.

INDUSTRIAL APPLICABILITY

According to the production method of the present invention, corneal endothelial substitute cells can be produced more efficiently from iPS cells. The corneal endothelial substitute cells obtained by the production method can be used as a medicament for the treatment of diseases caused by functional disorder of corneal endothelial cells, such as corneal sheet for corneal transplantation and the like, and for cell therapy for the treatment of such diseases.

This application is based on a patent application No. 2018-005076 filed in Japan (filing date: Jan. 16, 2018), the contents of which are incorporated in full herein.

The invention claimed is:

1. A medium for inducing a corneal endothelial substitute cell that expresses Na,K-ATPase a1 subunit (ATP1A1), ZO-1, N-cadherin, and PITX2 from a somatic cell derived induced pluripotent stem (iPS) cell that expresses Oct4, Lin28A, and Sox9, the medium comprising
  a basal medium selected from the group consisting of MEM medium, BME medium, BGJb medium, CMRL 1066 medium, Glasgow MEM medium, Improved MEM Zinc Option medium, IMDM medium, Medium 199 medium, Eagle MEM medium, aMEM medium, DMEM medium, ham medium, RPMI 1640 medium, Fischer's medium, a mixed medium thereof, and DMEM/F12 medium,
  a serum replacement,
  insulin-like growth factor 1 (IGF1),
  a signal transducer and activator of transcription 3 (STAT3) activator that is one or both of interleukin-6 (IL-6) and leukemia inhibitory factor (LIF),
  adrenal gland hormone selected from the group consisting of dexamethasone, hydrocortisone, betamethasone, beclomethasone, aldosterone, dehydroepiandrosterone, and androstenedione, and
  not comprising a basic fibroblast growth factor or a Rho-associated, coiled-coil-containing kinase (ROCK) inhibitor.

2. The medium according to claim 1, further comprising a keratinocyte growth factor.

3. The medium according to claim 1, further comprising transforming growth factor beta 1 (TGF-beta 1).

4. The medium according to claim 1, further comprising ascorbic acid.

5. The medium according to claim 1, wherein the basal medium is DMEM/F12 medium.

6. The medium according to claim 1, wherein the adrenal gland hormone is selected from the group consisting of aldosterone, dexamethasone, and hydrocortisone.

7. The medium according to claim 1, which is a medium comprising
  DMEM/F12 medium as a basal medium,
  insulin-like growth factor 1 (IGF1),
  a signal transducer and activator of transcription 3 (STAT3) activator that is one or both of interleukin-6 (IL-6) and leukemia inhibitory factor (LIF),
  dexamethasone, and
  aldosterone.

8. A method for producing a corneal endothelial substitute cell that expresses Na,K-ATPase a1 subunit (ATP1A1), ZO-1, N-cadherin, and PITX2 from a somatic cell derived induced pluripotent stem (iPS) cell that expresses Oct4, Lin28A, and Sox9, the method comprising adhesion-culturing in a medium comprising a basal medium selected from the group consisting of MEM medium, BME medium, BGJb medium, CMRL 1066 medium, Glasgow MEM medium, Improved MEM Zinc Option medium, IMDM medium, Medium 199 medium, Eagle MEM medium, aMEM medium, DMEM medium, ham medium, RPMI 1640 medium, Fischer's medium, a mixed medium thereof, and DMEM/F12 medium, a serum replacement, insulin-like growth factor 1 (IGF1), a signal transducer and activator of transcription 3 (STAT3) activator that is one or both of interleukin-6 (IL-6) and leukemia inhibitory factor (LIF), adrenal gland hormone selected from the group consisting of dexamethasone, hydrocortisone, betamethasone, beclomethasone, aldosterone, dehydroepiandrosterone, and androstenedione, and not comprising a basic fibroblast growth factor or a Rho-associated, coiled-coil-containing kinase (ROCK) inhibitor.

9. The method according to claim 8, wherein the medium further comprises a keratinocyte growth factor.

10. The method according to claim 8, wherein the medium further comprises transforming growth factor beta 1 (TGF-beta 1).

11. The method according to claim 8, further comprising ascorbic acid.

12. The method according to claim 8, wherein the basal medium is DMEM/F12 medium.

13. The method according to claim 8, wherein the adrenal gland hormone is selected from the group consisting of aldosterone, dexamethasone, and hydrocortisone.

14. The medium according to claim 8, which is a medium comprising

DMEM/F12 medium as a basal medium, insulin-like growth factor 1 (IGF1), a signal transducer and activator of transcription 3 (STAT3) activator that is one or both of interleukin-6 (IL-6) and leukemia inhibitory factor (LIF), dexamethasone, and aldosterone.

* * * * *